(12) United States Patent
Nakajima

(10) Patent No.: US 9,380,997 B2
(45) Date of Patent: Jul. 5, 2016

(54) ULTRASONIC DIAGNOSIS DEVICE

(75) Inventor: Shinji Nakajima, Mitaka (JP)

(73) Assignee: HITACHI ALOKA MEDICAL, LTD., Tokyo (JP)

(*) Notice: Subject to any disclaimer, the term of this patent is extended or adjusted under 35 U.S.C. 154(b) by 408 days.

(21) Appl. No.: 13/639,355

(22) PCT Filed: May 25, 2011

(86) PCT No.: PCT/JP2011/062015
§ 371 (c)(1),
(2), (4) Date: Oct. 4, 2012

(87) PCT Pub. No.: WO2011/148987
PCT Pub. Date: Dec. 1, 2011

(65) Prior Publication Data
US 2013/0030292 A1    Jan. 31, 2013

(30) Foreign Application Priority Data

May 27, 2010   (JP) ................................. 2010-121432

(51) Int. Cl.
*A47G 29/00*    (2006.01)
*A61B 8/00*    (2006.01)

(52) U.S. Cl.
CPC ............ *A61B 8/462* (2013.01); *A61B 8/4405* (2013.01); *A61B 8/463* (2013.01)

(58) Field of Classification Search
USPC .......................................................... 600/437
See application file for complete search history.

(56) References Cited

U.S. PATENT DOCUMENTS

| | | | |
|---|---|---|---|
| 4,625,731 A | 12/1986 | Quedens et al. | |
| 4,870,954 A | 10/1989 | Satoh | |
| 5,129,397 A | 7/1992 | Jingu et al. | |
| 5,867,148 A * | 2/1999 | Kamimaki et al. | 345/169 |
| 6,682,157 B2 | 1/2004 | Ito | |
| 6,709,391 B2 | 3/2004 | Mesaros et al. | |
| 6,746,402 B2 * | 6/2004 | Ustuner | 600/462 |

(Continued)

FOREIGN PATENT DOCUMENTS

| | | |
|---|---|---|
| CN | 2613958 Y | 4/2004 |
| CN | 1655722 A | 8/2005 |

(Continued)

OTHER PUBLICATIONS

Extended European Search Report dated Mar. 6, 2013, issued in corresponding European Patent Application No. 11786688.9.

(Continued)

*Primary Examiner* — Tse Chen
*Assistant Examiner* — Lisa Kinnard
(74) *Attorney, Agent, or Firm* — Westerman, Hattori, Daniels & Adrian, LLP

(57) ABSTRACT

An ultrasonic diagnosis device wherein, in order to reliably stop the movement of a display unit by a simple mechanism during transportation of the device, a display unit restraint mechanism is provided with: a fixed portion which has a receiving groove for receiving a handle main unit provided on the display unit; and a rotation portion which moves rotationally in relation to the fixed portion. When the rotation portion is rotated with the handle main unit received in the receiving groove, the upper side of the handle main unit becomes covered with a cover portion. In this state, a hook member protrudes outward from the rotation portion and is engaged with an upper end portion to serve as a strut.

7 Claims, 25 Drawing Sheets

(56) References Cited

U.S. PATENT DOCUMENTS

| | | | |
|---|---|---|---|
| 7,594,728 B2* | 9/2009 | Seal et al. ..................... 351/210 |
| 7,999,987 B2 | 8/2011 | Namose |
| 2002/0190609 A1 | 12/2002 | Takeuchi et al. |
| 2003/0025054 A1 | 2/2003 | Toennesland et al. |
| 2003/0220564 A1 | 11/2003 | Wilkins et al. |
| 2003/0220565 A1 | 11/2003 | Mesaros et al. |
| 2003/0220571 A1 | 11/2003 | Mesaros et al. |
| 2004/0068185 A1* | 4/2004 | Marshall et al. ............... 600/437 |
| 2006/0241435 A1 | 10/2006 | Koga et al. |
| 2007/0051861 A1 | 3/2007 | Teramachi et al. |
| 2007/0067792 A1 | 3/2007 | Kitagawa et al. |
| 2007/0132894 A1* | 6/2007 | Vitito ............................ 348/837 |
| 2008/0035802 A1* | 2/2008 | Kim ......................... 248/123.11 |
| 2008/0115607 A1 | 5/2008 | Chang et al. |
| 2008/0132786 A1 | 6/2008 | Asai et al. |
| 2008/0228071 A1 | 9/2008 | Mesaros |
| 2008/0234577 A1 | 9/2008 | Murkowski et al. |
| 2009/0212133 A1 | 8/2009 | Collins, Jr. |
| 2009/0223033 A1 | 9/2009 | Houser |
| 2010/0094130 A1 | 4/2010 | Ninomiya et al. |
| 2010/0152588 A1 | 6/2010 | Ninomiya et al. |

FOREIGN PATENT DOCUMENTS

| | | |
|---|---|---|
| CN | 2814617 Y | 9/2006 |
| CN | 1846629 A | 10/2006 |
| CN | 1917815 A | 2/2007 |
| CN | 101047038 A | 10/2007 |
| CN | 201039832 Y | 3/2008 |
| CN | 101202123 A | 6/2008 |
| CN | 101203100 A | 6/2008 |
| CN | 100506165 C | 7/2009 |
| CN | 100518661 C | 7/2009 |
| CN | 101541246 A | 9/2009 |
| CN | 201404228 Y | 2/2010 |
| EP | 2092892 A1 | 8/2009 |
| JP | 63-009429 A | 1/1988 |
| JP | 1-0176407 U | 12/1989 |
| JP | 03-109620 A | 5/1991 |
| JP | 05-015529 A | 1/1993 |
| JP | 6-90951 A | 4/1994 |
| JP | 08-140970 A | 6/1996 |
| JP | 2003-144433 A | 5/2003 |
| JP | 2004-000624 A | 1/2004 |
| JP | 2007-97775 A | 4/2004 |
| JP | 2005-526566 A | 9/2005 |
| JP | 2007-021088 A | 2/2007 |
| JP | 2007-520304 A | 7/2007 |
| JP | 2007-520305 A | 7/2007 |
| JP | 2008-126015 A | 6/2008 |
| JP | 2008-142331 A | 6/2008 |
| JP | 2009-125371 A | 6/2009 |
| JP | 2009-136692 A | 6/2009 |
| JP | 2009-254725 A | 11/2009 |

OTHER PUBLICATIONS

Extended Search Report dated Oct. 18, 2013, issued in European Patent Application No. 11786685.5 (5 pages).
International Search Report dated Jul. 12, 2011, issued in corresponding application No. PCT/JP2011/062015.
Notification Concerning Transmittal of International Preliminary Report on Patentability (Form PCT/IB/326) of related International Patent Application No. PCT/JP2011/062017 dated Dec. 6, 2012, with Forms PCT/IB/373 and PCT/ISA/237.
Notification of Transmittal of Translation of the International Preliminary Report on Patentability (Form PCT/IB/338) of related International Patent Application No. PCT/JP2011/062017 dated Dec. 13, 2012, with Forms PCT/IB/373 and PCT/ISA/237.
Second and Supplementary Notice Informing the Applicant of the Communication of the International Application (Form PCT/IB/308) of related International Patent Application No. PCT/JP2011/062017, dated Sep. 27, 2012.
International Search Report of related PCT/JP2011/062016, mailing date of Jul. 12, 2011.
Notification of Transmittal of Translation of the International Preliminary Report on Patentability (Form PCT/IB/338) of related International Patent Application No. PCT/JP2011/062016, dated Dec. 20, 2012, with Form PCT/IPEA/409.
Second and Supplementary Notice Informing the Applicant of the Communication of the International Application (Form PCT/IB/308) of related International Patent Application No. PCT/JP2011/062016, dated Sep. 27, 2012.
International Search Report dated Jul. 12, 2011, issued in related application No. PCT/JP2011/062014.
Notification of Transmittal of Translation of the International Preliminary Report on Patentability (Form PCT/IB/338) of related International Patent Application No. PCT/JP2011/062014, dated Dec. 13, 2012, with Forms PCT/IB/373 and PCT/ISA/237.
Notification Concerning Transmittal of International Preliminary Report on Patentability Form PCT/IB/326 of related International Patent Application No. PCT/JP2011/062014 dated Dec. 6, 2012, with Forms PCT/IB/373 and PCT/ISA/237.
Second and Supplementary Notice Informing the Applicant of the Communication of the International Application (Form PCT/IB/308) of related International Patent Application No. PCT/JP2011/062014, dated Sep. 27, 2012.
International Search Report of related PCT/JP2011/062017, mailing date of Jul. 12, 2011.
Notification of Transmittal of Translation of the International Preliminary Report on Patentability (Form PCT/IB/338) of International Patent Application No. PCT/JP2011/062015, dated Dec. 13, 2012, with Forms PCT/IB/373 and PCT/ISA/237.
Notification Concerning Transmittal of International Preliminary Report on Patentability Form PCT/IB/326 of International Patent Application No. PCT/JP2011/062015 dated Dec. 6, 2012, with Forms PCT/IB/373 and PCT/ISA/237.
Second and Supplementary Notice Informing the Applicant of the Communication of the International Application (Form PCT/IB/308) of the International Patent Application No. PCT/JP2011/062015, dated Sep. 27, 2012.
Chinese Office Action dated Jun. 4, 2014, issued in Chinese Patent Application No. 201180026310.5 with English translation (17 pages) (this doccument is corresponding to U.S. Appl. No. 13/639,371).
Chinese Office Action dated May 23, 2014, issued in Chinese Patent Application No. 201180026312.4 with English translation (16 pages) (this doccument is corresponding to U.S. Appl. No. 13/639,305).
Chinese Office Action dated May 6, 2014, issued in corresponding Chinese Patent Application No. 201180026317.7 with English translation (11 pages).
Chinese Office Action dated Apr. 29, 2014, issued in Chinese Patent Application No. 201180026286.5 with English translation (11 pages) (corresponding to U.S. Appl. No. 13/639,307).
U.S. Non-Final Office Action dated Jun. 20, 2014, issued in related U.S. Appl. No. 13/639,307 (38 pages).
Chinese Office Action dated Nov. 27, 2014, issued in corresponding Chinese Patent Application No. 201180026317.7, with English Translation (17 pages).
Extended European Search Report dated Jul. 30, 2015, issued in counterpart European Patent Application No. 11786686.3 (5 pages).

* cited by examiner

ULTRASONIC DIAGNOSIS DEVICE

TECHNICAL FIELD

The present invention relates to an ultrasonic diagnosis device, and more particularly to an operation panel and a support mechanism thereof.

BACKGROUND ART

Ultrasonic diagnosis devices used in the field of medicine generally include a main unit (a cart), and an operation panel supported on the main unit. The main unit houses a plurality of electronic circuit boards and power source sections. A plurality of casters are provided on a bottom portion of the main unit. The operation panel generally includes a switch, a pointing device, a rotary knob, a sub display, or the like. A display unit may be mounted on the operation panel via an arm mechanism. In such a structure, the operation panel, the arm mechanism, and the display unit constitute a movable section.

When the movable section as described above is constituted, during transportation of an ultrasonic diagnosis device (during transportation within a hospital, transportation by a vehicle, or the like), it is necessary to stop the movement of each of the members constituting the movable section, in view of safety and device protection. Specifically, it is desired to lock the position and attitude of the operation panel in order to inhibit the operation panel from performing a horizontal movement, and it is also desired to lock the position and attitude of the display unit in order to inhibit the display unit from performing a horizontal movement and a vertical movement. The movement of the operation panel can be inhibited by operating a lock mechanism provided in a support mechanism that supports the operation panel. The movement of the display unit is conventionally inhibited directly by stopping the operation of each portion constituting the arm mechanism (see Patent Literatures 1 to 4). During times other than transportation, such as during maintenance including cleaning of the display surface, for example, it may also be necessary to forcedly stop the operation of the display unit.

PRIOR ART DOCUMENTS

Patent Literatures

Patent Literature 1: JP 2007-97775 A
Patent Literature 2: JP 2008-142331 A
Patent Literature 3: JP 2009-125371 A
Patent Literature 4: JP 2009-136692 A

SUMMARY OF THE INVENTION

Problems to be Solved by the Invention

In a state in which two arms of the arm mechanism are stacked in the vertical direction, it is possible to stop the movement of the two arms by providing a certain member across these two arms. In this case, however, it is not possible to stop any movements that are performed ahead of the two arms; more specifically, a tilt movement or a pivot movement of the display unit. By providing a mechanism for stopping the movement at each movable portion whose operation needs to be stopped, the movement of the whole arm mechanism can be completely stopped, so that the position and attitude of the display unit can be held. However, as such a structure requires a complicated mechanism or a large number of components in order to lock the movement of the display unit, there arise problems of complication of the device structure and an increase in costs.

Further, in the field of ultrasonic diagnosis devices, in recent years flat panel displays have frequently been used. Such a display unit generally includes, on a front face thereof, a handle that is operated by a user to adjust the position and orientation thereof. Such a handle has a shape that allows the user to easily set the position and orientation of the display unit while holding the handle, and also has a sufficient strength that can resist such an operation. There is also a trend toward large size flat panel displays, and implementation of a means that reliably stops the movement of such a large display unit has been demanded.

An advantage of the present invention is to provide an ultrasonic diagnosis device, in which the movement of the display unit can be stopped with a simple mechanism.

Solution to Problems

Preferably, an ultrasonic diagnosis device includes an operation panel including a plurality of input units for ultrasonic diagnosis, a base that is provided on a back side of the operation panel, an arm mechanism that is mounted on the base, a display unit that is movably supported by the arm mechanism and includes a handle that is to be held by a user, and a display unit restraint mechanism that is provided on the base or the operation panel to detachably hold the handle to thereby restrain the display unit.

With the above structure, the handle provided on the display unit is held by the display unit restraint mechanism, so that the display unit is directly restrained. In this case, the operation of the arm mechanism may be additionally locked or may not be locked. In other words, with the above structure, as the movement of the display unit itself can be limited without forcedly stopping the movements of a plurality of moving mechanisms of the arm mechanism individually, the display unit itself can be protected. As the handle is a member that is used by a user to operate the display unit and therefore has a predetermined strength or rigidity, the method of fixing the display unit by holding the handle, albeit primitive, is an extremely reasonable method. Specifically, as it is only necessary to hold the handle, the display unit can be restrained by a simple mechanism.

Preferably, the handle includes a rod-like handle main unit provided on a lower portion on a front surface side of the display unit and extending along a left-right direction of the display unit, and the display unit restraint mechanism includes a handle groove that is opened upwardly for receiving the handle main unit, and a cover member that covers over an upper side of the handle main unit when the handle main unit is fitted into the handle groove. With this structure, it is possible to complete positioning of the handle only by fitting the rod-like handle main unit into the handle groove from above. By covering the upper side of the handle main unit with the cover member in this state, a stable retained state can be established while preventing removal of the handle. As the handle main unit is in a rod shape, for example, it is desirable to form the cover member in a columnar shape and allow the cover member to perform a rotation movement. In the direction across the handle main unit, the whole part of the handle main unit may be covered with the cover member, or a portion of the handle main unit may be covered. Various modes of the cover member can be adopted, so long as the cover member can exert an effect for inhibiting removal of the handle main unit from the handle groove. For example, the cover member can be formed of an elastic member. In such a structure, the cover member itself does not move, but deforms to allow passage of the handle main unit when the handle main unit is inserted into the handle groove and when the handle main unit is extracted from the handle groove. In a state in which the handle main unit is inserted into the handle groove, the cover member naturally protrudes over the upper portion of the handle main unit to thereby establish a restraint state of the handle main unit.

Preferably, the display unit restraint mechanism further includes a restriction member that restricts return of the cover member when the cover member is in a covering state in which the cover member covers over the upper side of the handle main unit. With this structure, as the restriction member can prevent return movement of the cover member, the restraint state of the display unit can be maintained in a stable manner even if vibrations or the like arise in the ultrasonic diagnosis device.

Preferably, the operation panel is composed of a first operation section provided on a front side and a second operation section that stands upright from a back side of the first operation section, the base includes an extension end that is coupled with a rear surface of the second operation section, and the display unit restraint mechanism is disposed in a space formed between an upper surface of the extension end and the rear surface of the second operation section. With this structure, it is possible to make use of a dead space and also to enhance the appearance of the device, because the whole portion or a portion of the display unit restraint mechanism can be put out of the user's sight. However, the back side of the operation panel can be visually recognized in the state that the user is standing, and the user can easily insert his/her hand into the space.

Preferably, the restriction member restricts a returning movement of the cover member by mechanically coupling the cover member in the covering state with an upper portion of the second operation section. With this structure, it is possible to allow the upper end portion of the operation panel to play an additional role and to make full use of a triangular space or structure formed between the upper end portion and the base.

Preferably, the cover member is a member that performs a rotation movement about a horizontal center axis, the restriction member is housed in the cover member in an unactuated state thereof and protrudes outward from within the cover member to serve as a strut between the cover member and the upper portion of the second operation section, and there is provided an urging member for urging the restriction member in a protruding direction.

Preferably, an ultrasonic diagnosis device includes a main unit that houses an electronic circuit for ultrasonic diagnosis, an arm mechanism that is provided on the main unit, a display unit that is movably supported by the arm mechanism and includes a handle that is to be held by a user, and a display unit restraint mechanism that is provided on the main unit or a movable member movably supported by the main unit, the display unit restraint mechanism detachably holding the handle to restrain the display unit. Preferably, the main unit is a cart provided with a plurality of casters, and the arm mechanism (a support mechanism) is provided directly on a top face or the like of the main unit to thereby support the display unit. The handle of the display unit is mechanically held by the display unit restraint mechanism, so that the display unit is restrained. The display unit restraint mechanism is provided on the main unit or on a movable section (preferably the operation panel or a structure continuous to the operation panel) that is movably supported on the main unit. In the former case, the display unit restraint mechanism is provided on the top face of the main unit, for example. In the latter case, it is desirable to provide a lock mechanism on the movable section for stopping the movement of the movable section. More specifically, it is desirable to make the display unit restraint mechanism function while the movable section is in a locked state. In a modification example of the embodiment as will be described in detail below, the arm mechanism may be disposed directly on the main unit illustrated in FIG. 1 or the like. In such an aspect, the display unit restraint mechanism is provided on the main unit or the movable section. In any case, a common technical feature can be recognized in that the handle of the display unit is used for mechanically restraining the display unit.

Advantageous Effects of the Invention

According to the present invention, it is possible to stop the movement of the display unit with a simple mechanism by using the handle provided on the display unit.

MODE FOR CARRYING OUT THE INVENTION

Preferred embodiments of the present invention will now be described with reference to the drawings.

(1) Basic Structure of an Ultrasonic Diagnosis Device (FIGS. 1 to 4)

Figure 1:
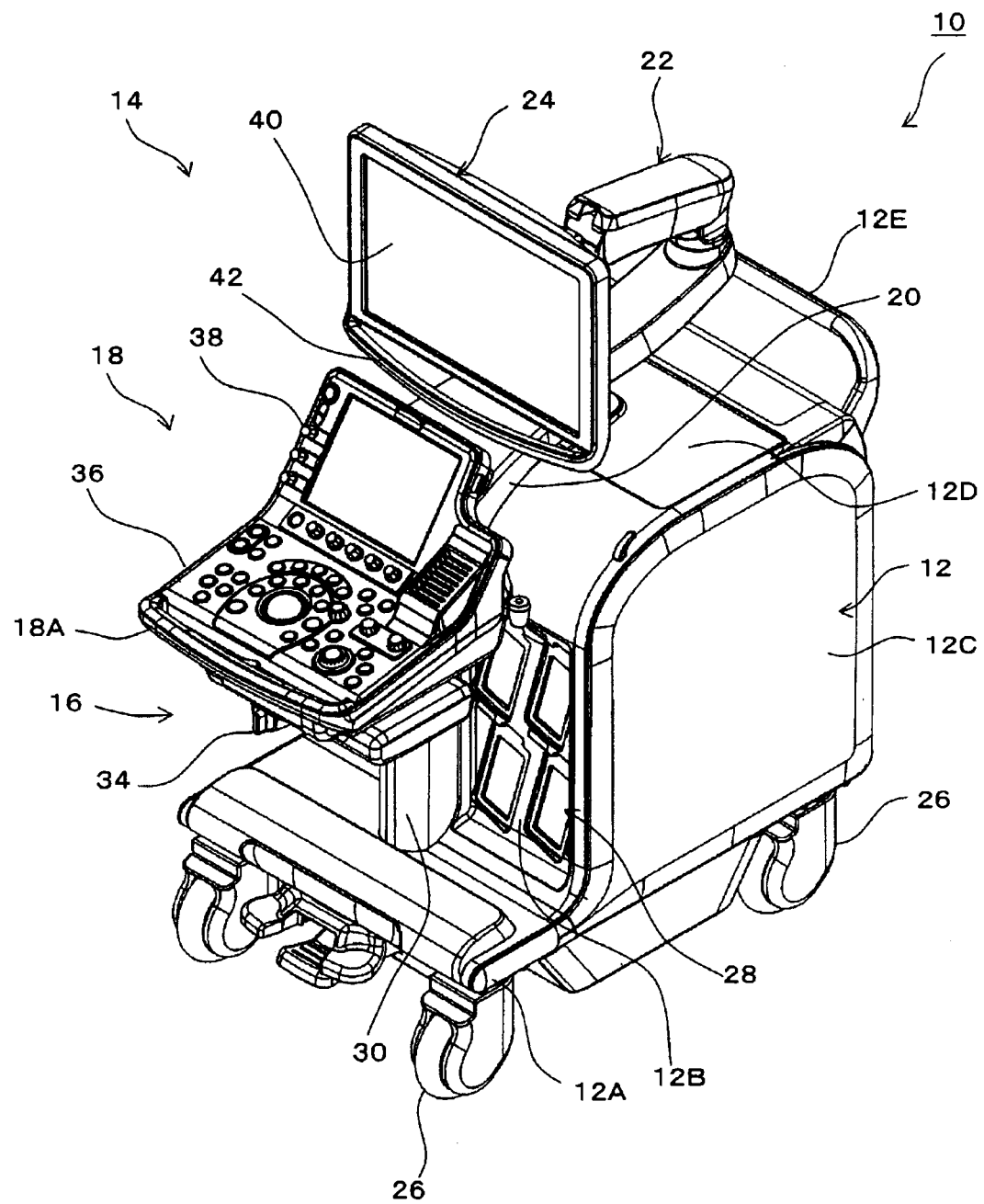
FIG. 1 First perspective view illustrating an ultrasonic diagnosis device according to an embodiment of the present invention.

FIG. 1 illustrates a preferred embodiment of an ultrasonic diagnosis device according to the present invention. This ultrasonic diagnosis device, which is used in the field of medicine, performs transmission/reception of ultrasound with respect to a living organism (particularly, a human body) captures a received signal, and forms an ultrasonic image based on the received signal.

The ultrasonic diagnosis device 10 includes a main unit 12, a movable section 14, and a movable mechanism 16. The main unit 12 has a box shape and houses therein a plurality of electronic circuit boards and power source sections. The lower part of the main unit 12 protrudes slightly forward to form a main unit base 12A. Four casters 26 are provided under the main unit base 12A. The projection portion of the main unit base 12A functions as a footrest on which a foot is placed. The main unit 12 includes a front face 12B, a side face 12C, and a top face 12D. A rounded convex corner surface is formed from the front face 12B over to the top face 12D. A connector unit 28 formed of a plurality of main unit side connectors is provided on the front face 12B.

A probe is to be removably mounted to each main unit side connector. More specifically, a probe is composed of a probe connector (a connector box), a probe cable, and a probe head. The probe connector is mounted to one of the main unit side connectors. A support column, which will be described below, is provided on the main unit base 12A, and is covered with a column cover 30. The support column is provided on the front face side of the unit 12, in the center in the left-right direction. A handle 12E is provided on the backward end of the main unit 12.

As will be described below, the movable mechanism 16 includes a lifting mechanism, a left-right slide mechanism, a forward-backward slide mechanism, and a rotation mechanism. The left-right slide mechanism, the forward-backward slide mechanism, and the rotation mechanism are provided in a layered structure and together form a horizontal movement mechanism. In FIG. 1, reference numeral 34 indicates a knob that constitutes a part of a home position lock mechanism.

In the present embodiment, the movable section 14 is composed of an operation panel 18, a base 20, an arm mechanism 22, and a display unit 24. The operation panel 18 is composed of a first operation section 36 and a second operation section 38 provided to rise from the back side of the first operation section 36. The first operation section 36 has a first operation surface, and the second operation section 38 has a second operation surface. A plurality of switches or the like are arranged on the first operation surface, and a sub display or the like is provided on the second operation surface. The angle of inclination of the second operation surface is larger than that of the first operation surface. A handle 18A is provided on the front side of the first operation section 36. This handle 18A also serves as a palm rest on which a wrist or a portion near the wrist is placed.

On the back side of the operation panel 18, the base 20 extending in the depth direction is provided, and the arm mechanism 22 is mounted on the base 20. The arm mechanism 22 is a mechanism for varying the position and attitude (orientation) of the display unit 24. The display unit 24 is formed as a flat panel display, and reference numeral 40 indicates a display unit main body. A handle 42 having an arc shape is provided on the lower portion on the front surface of the display unit main body 40. A user can hold the handle 42 to position the display unit 24 or direct the display unit 24 at a desired attitude. Further, by holding the handle 18A to move the handle 18A in the horizontal direction, the position of the movable section 14 in the left-right direction and the forward-backward direction can be determined and also the movable section 14 can be rotated about a predetermined rotation axis. Also, on the upper surface of an attachment end of the base 20, on the back side of the second operation section 38, a display unit restraint mechanism is provided.

Figure 2:
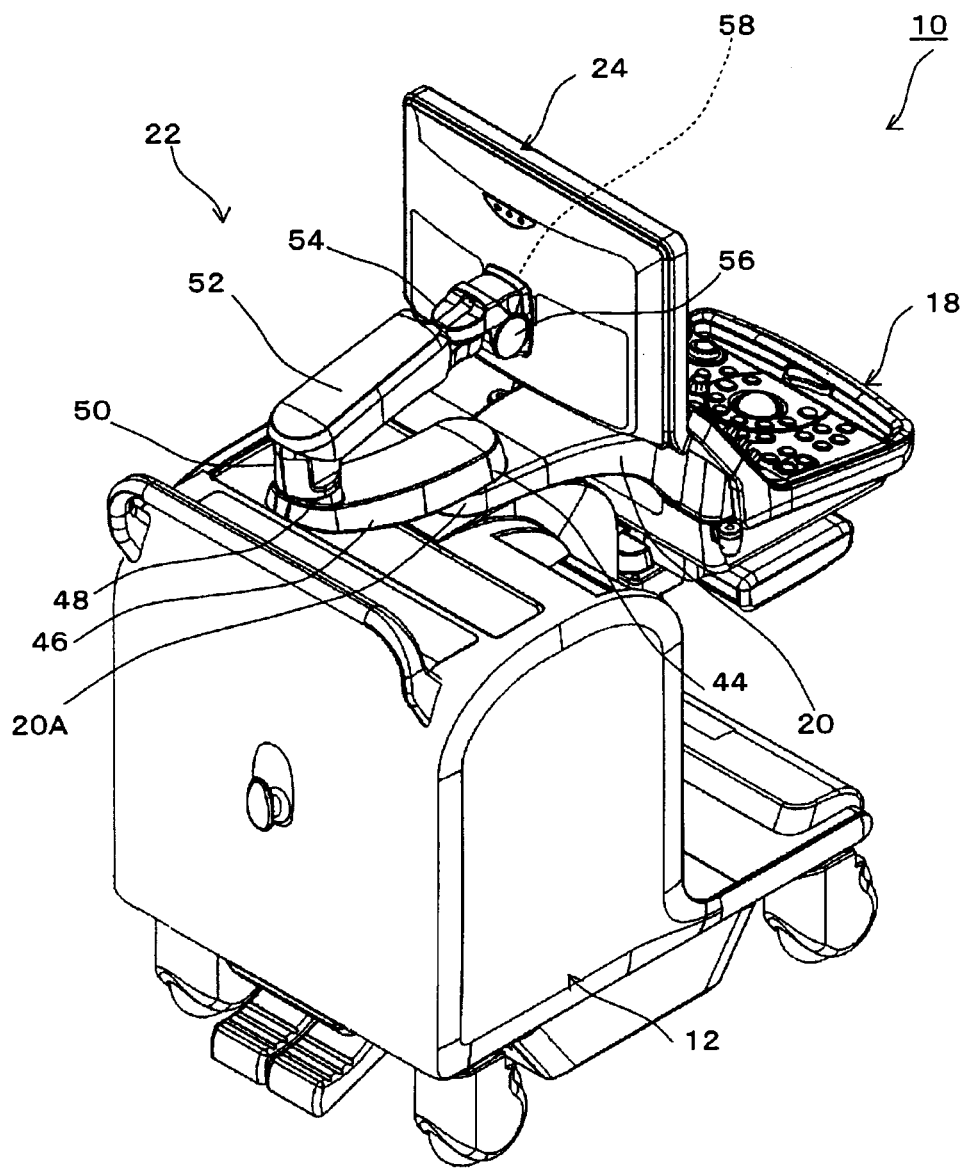
FIG. 2 Second perspective view illustrating the ultrasonic diagnosis device according to the embodiment.

FIG. 2 illustrates the ultrasonic diagnosis device illustrated in FIG. 1 as viewed obliquely from the back. As described above, the ultrasonic diagnosis device 10 includes the movable section which includes the operation panel 18, the base 20, the arm mechanism 22, and the display unit 24. The movable section is supported by the main unit 12. More specifically, the movable section is supported by the main unit 12 via the movable mechanism, which will be described below.

The arm mechanism 22 will be described in detail. On the backward end 20A of the base 20, a first pivot portion 44 is provided. One end of a first arm 46 is mounted on the first pivot portion 44, and a second pivot portion 48 is mounted on the other end of the first arm 46. An intermediate arm 50 which stands upright and has a short length is mounted on the second pivot portion 48, and an upper end of the intermediate arm 50 is coupled to one end of a second arm 52. The second arm 52 is an arm having parallel links capable of an inclined movement, and a third pivot portion 54 is provided on the other end of the second arm 52. Further, a tilt portion 56 is provided between the third pivot portion 54 and the display unit 24, and an attitude correction mechanism 58 which will be described below is provided between the tilt portion 56 and the display unit 24.

The first arm 46 is a horizontal arm, and the other end portion of the first arm 46 is warped slightly upward. In the arm mechanism 22, the elements from the first pivot portion 44 to the tilt portion 56 form an arm mechanism main unit, and the attitude correction mechanism 58 is provided further to the arm mechanism main unit. As will be described below, the attitude correction mechanism 58 is a mechanism that cancels, when the end portion of the arm mechanism 22 on the display unit side droops down to make the display unit 24 appear to be inclined or rotated, such an inclination or rotation of the display unit 24.

Figure 3:
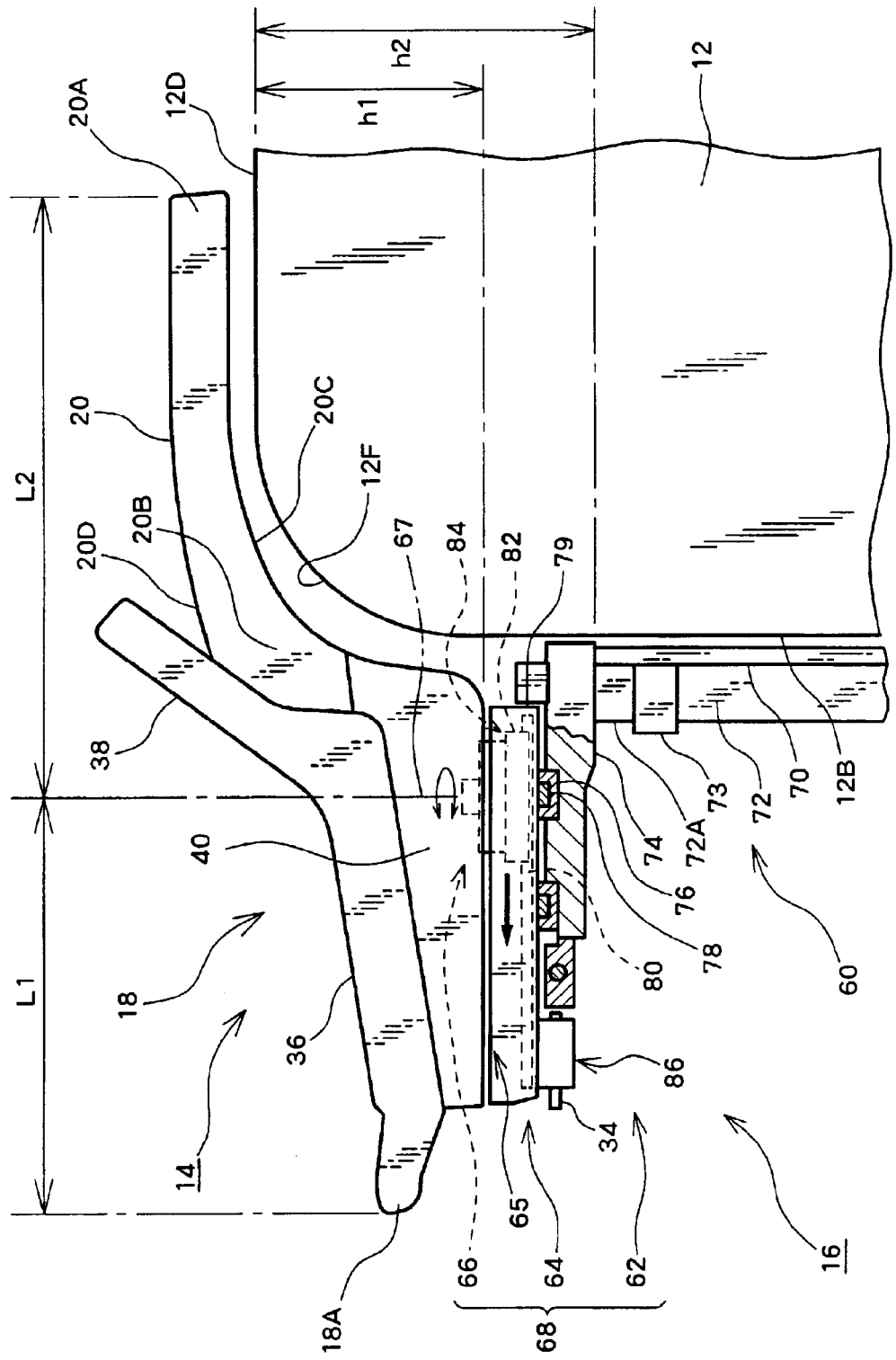
FIG. 3 Side view schematically illustrating a movable mechanism that changes the position and attitude of a movable section.

FIG. 3 illustrates the principle of the movable mechanism 16. FIG. 3 illustrates a schematic structure, and the details of each mechanism will be illustrated in FIG. 5 and subsequent drawings. As described above, the main unit 12 includes the front face 12B and the top face 12D, and the rounded convex corner face 12F is formed from the front face 12B over to the top face 12D. The movable mechanism 16 has a lifting mechanism 60 and a horizontal movement mechanism 68. The horizontal movement mechanism 68 includes a left-right slide mechanism 62, a forward-backward slide mechanism 64, and a rotation mechanism 66. These mechanisms are stacked to form a layered structure, as described above.

The lifting mechanism 60 includes a support column formed of a fixed column 70 and a movable column 72. The movable column 72 is held by the fixed column 70 in a manner that the movable column 72 can move in the upward-downward direction. Reference numeral 73 indicates a holding member for this purpose. A movable base 74 that performs an up-down movement is coupled to an upper end portion 72A of the movable column 72. The movable base 74 is a horizontal plate that expands toward the forward direction from the upper end portion 72A.

The left-right slide mechanism 62 is mounted on the movable base 74. The left-right slide mechanism 62 includes a pair of rails 78 arranged in the front-back direction, and a pair of rail slots 76 that receive the rails 78 for allowing slide movement thereof in the left-right direction. Here, reference numeral 86 indicates the home position lock mechanism that includes a knob 34. The details of the home position lock mechanism 86 will be described below.

The forward-backward slide mechanism 64 includes a center case 79 having a bottom surface which is a left-right slide base. On the left-right slide base, a pair of rails 80 are arranged side by side in the left-right direction. A slider 82 is mounted on the pair of rails 80. The slider 82 constitutes a forward-backward slide base, on which the rotation mechanism 66 is mounted. Here, a rotation limitation mechanism which will be described below is provided between the left-right slide base and the operation panel 18. Further, a shutter mechanism 84 is provided for opening/closing an opening portion formed on the upper surface side of the center case 79, as will also be described in detail below. The rotation mechanism 66 is a mechanism that allows the operation panel 18; i.e. the movable section 14, to rotate about a rotation center axis 67. The rotation center axis 67 is specifically positioned at a sliding position in the left-right and forward-backward directions (a two-dimensional position), which is defined by the left-right slide mechanism 62 and the forward-backward slide mechanism 64.

As described above, the operation panel 18 includes the first operation section 36 and the second operation section 38, and also includes the handle 18A provided on the front surface side. On the bottom wall of the operation panel 18, a rotation member (rotor) of the rotation mechanism 66 is coupled. The base 20 includes an attachment portion 20B and a rear end portion 20A. The attachment portion 20B is coupled to the operation panel 18 at an intermediate location on the back surface side thereof, and the base 20 extends therefrom toward the depth side, with the end portion of the base 20 being the rear end portion 20A. A display unit restraint mechanism, which will be described below, is placed on an upper surface 20D of the attachment portion 20B. The lower surface 20C of the base 20 is curved to have a concave shape as viewed from the side surface direction.

In FIG. 3, the movable section 14 is in a home position. More specifically, the movable section 14 is located at the lowermost end, the backward end, and the center position in the left-right direction, with the rotation angle being 0 degrees. In such a case, with respect to the rounded convex corner face 12F formed from the front face 12B over to the top face 12D of the main unit 12, the lower surface 20C, which is a similarly rounded concave curved surface, is in a close position. With such a positional relationship between these members, it is possible to avoid collision of the movable section 14 with the main unit 12 and also to position the operation panel 18 on the front face side of the main unit 12 at a lowest possible location.

In FIG. 3, the length from the rotation center axis 67 to the front end of the operation panel 18 is indicated as L1, and the length from the rotation center axis 67 to the rear end of the base 20 is indicated as L2. As illustrated, L2 is greater than L1. Accordingly, the operation panel 18 can be turned in a small radius even when the movable section is rotated, whereas with the rotation of the base 20 in a large radius, the region within which the display unit can move can be expanded. Here, the distance from the top face 12D to the lowermost position of the operation panel 18 is indicated as h1, and the distance from the top face 12D to the lower surface position of the movable base 74 is indicated as h2. In the present embodiment, because the lowermost position of the operation panel 18 can be lowered and also the thickness of the horizontal movement mechanism 68 is made small, as indicated by h1 and h2, it is possible to form a large space under the horizontal movement mechanism 68 at all occasions. As the support column and the movable base 74 form an inverted L shape as viewed from the side face, in combination with such a configuration, it is possible to form a sufficient space under the horizontal movement mechanism 68. The user's foot and the like can be placed in such a space.

As described above, the horizontal movement mechanism 68 has a layered structure. From this point of view, the movable base 74 forms the lowermost layer, the left-right slide base forms a lower layer, the forward-backward slide base forms an intermediate layer, and the rotation base forms an upper layer. Then, the bottom wall of the operation panel 18 forms the uppermost layer. In this embodiment, with such a layered structure being assumed as a precondition, rotation limitation or the like can be attained with a simple mechanism. This will be described below.

Figure 4:
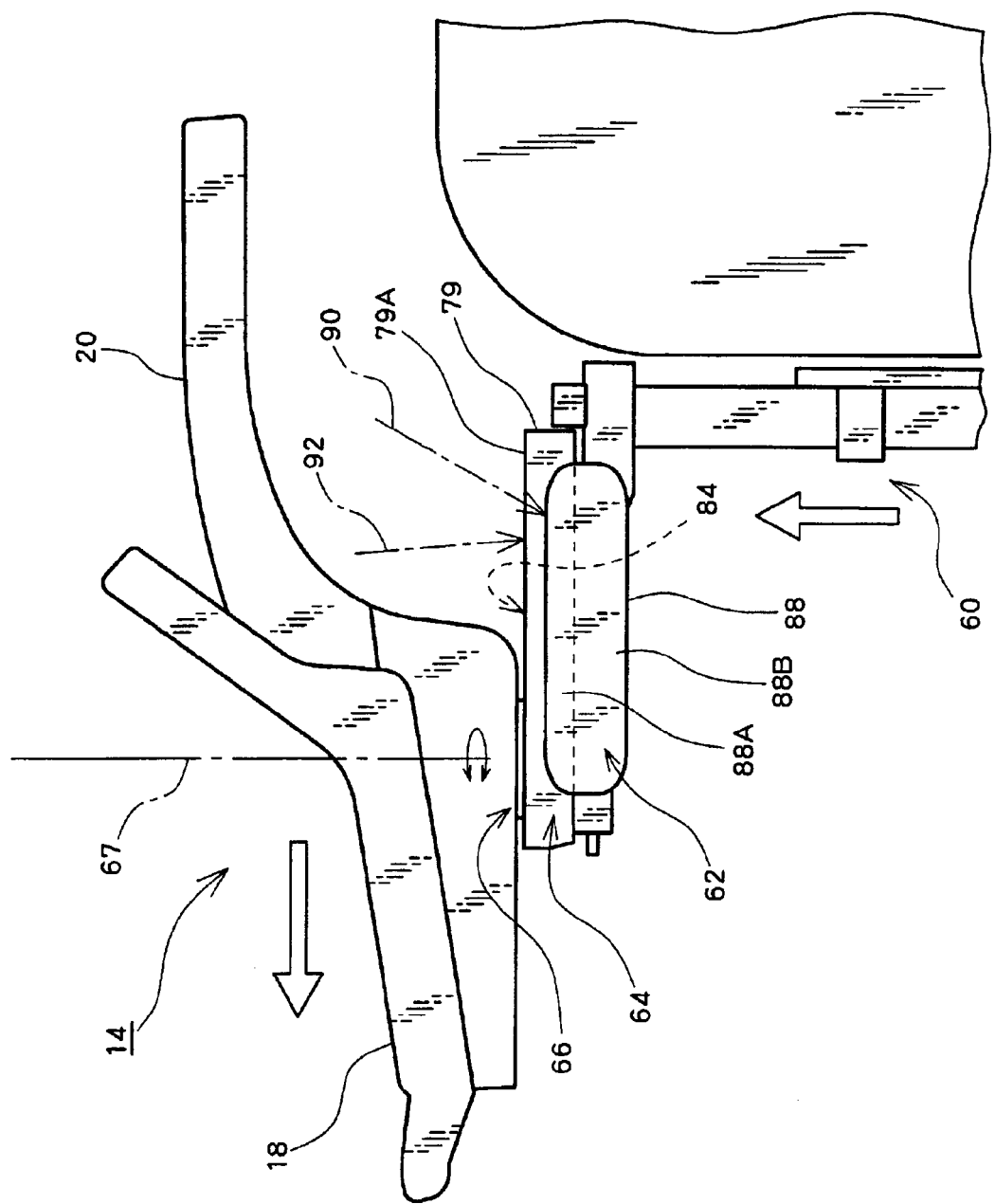
FIG. 4 Side view schematically illustrating a state in which the operation panel moves upward and forward.

FIG. 4 illustrates the movable section 14 which is located at the lifted position and is also at the forward end. Here, the rotation angle of the movable section 14 is 0 degrees. The center case 79 houses therein the forward-backward slide mechanism 64 and the main portions of the rotation mechanism 66. A side case 88 is provided on each of the right and left sides of the center case 79. These side cases 88 cover right and left end portions of the left-right slide mechanism 62, and each side case 88 is specifically formed of an upper cover 88A and a lower cover 88B. The side cases 88 are fixed to the center case 79 and move in the left and right directions with the left-right movement of the center case 79. Here, it is possible to form the side cases 88 integrally with the center case 79.

The upper surface of the center case 79 is opened, and the center portion thereof serves as a passage for the rotation member in the rotation mechanism 66. When the movable section 14 is positioned at the forward end, a large opening portion 79A is to be exposed on the rear side of the operation panel 18. However, such an exposure of the opening portion 79A would deteriorate the appearance and would also cause problems such as poor safety or entry of foreign matter. Accordingly, in the present embodiment, a shutter mechanism, which will be described below, is provided. By closing the opening portion 79A, which is exposed, with such a shutter mechanism 84, foreign matter externally entering as indicated by reference numeral 92 can be blocked. As the left-right slide mechanism 62 is covered with the side cases 88 as described above, this mechanism is also protected from an external force or the like, as indicated by reference numeral 90.

As described above, in the present embodiment, the various mechanisms are covered with the center case 79 and the side cases 88, which results in an increase in safety or the like. Further, the opening portion which is necessarily formed with the forward movement of the operation panel 18 can be specially closed by the shutter mechanism 84.

(2) Movable Mechanism (FIGS. 5 to 13)

Figure 5:
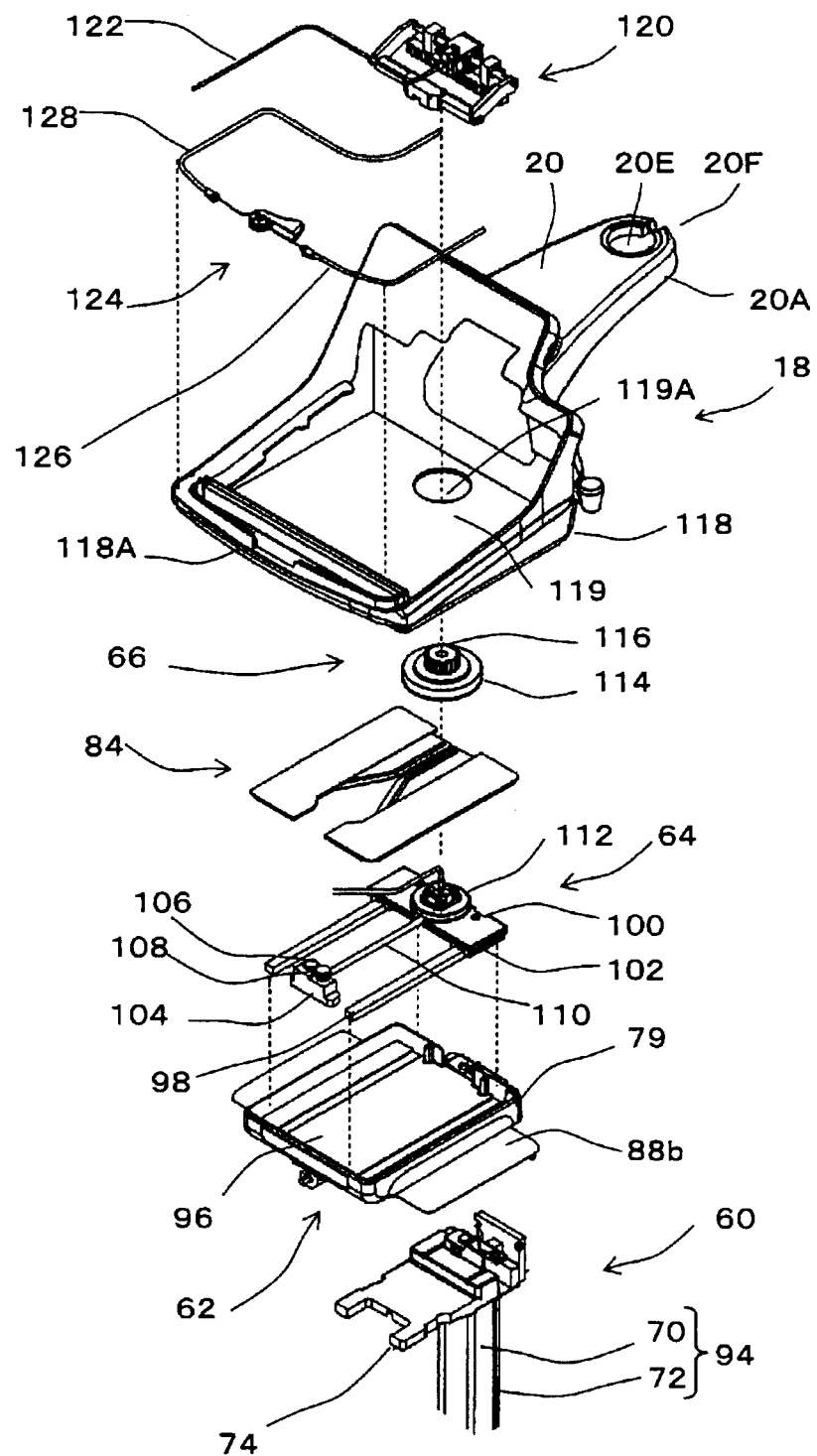
FIG. 5 First exploded perspective view illustrating the movable mechanism as viewed obliquely from above.

Next, the movable mechanism will be described in detail with reference to FIGS. 5 and 6. First, FIG. 5 will be referenced.

As described above, the lifting mechanism 60 includes the support column 94 and the movable base 74. The support column 94 is composed of the fixed column 70 and the movable column 72. The left-right slide mechanism 62 includes the center case 79, and a pair of upper portions 88a forming a portion of the side cases are provided on the right and left sides of the center case 79. Lower portions of the side case are omitted in the drawing. The center case and the side cases together form a mechanism case. The bottom wall of the center case 79 is the left-right slide base 96.

The forward-backward slide mechanism 64 includes a pair of forward-backward slide rails 98 that are members extending in the forward-backward direction. A forward-backward slide base 100 is mounted on the pair of forward-backward slide rails 98. Specifically, the forward-backward slide base 100 is provided on a pair of forward-backward sliders 102 such that the forward-backward slide base 100 can move in the forward-backward direction. More specifically, on the left-right slide base 96, the pair of forward-backward slide rails 98 is fixed, and also a block 104 and a guide shaft 110 are fixed. The block 104 includes projecting portions 106 and 108, as will be described below. The projecting portions 106 and 108 are rollers that constitute a portion of the rotation limitation mechanism.

The rotation mechanism 66 includes a non-rotational base (stator) 112, a rotor (a rotational base serving as a rotor) 114, and a non-rotational gear 116. The rotor 114 performs a rotational movement about the rotation center axis and is coupled to a bottom wall 119 of the operation panel 18. The non-rotational base 112 and the non-rotational gear 116 are coupled integrally. The upper surface of the center case 79 is opened and serves as a space for movement of the assembly including the rotor 114. The shutter mechanism 84 is provided so as to close such an opening portion as required. While the shutter mechanism 84 is in a closed state in FIG. 5, the shutter mechanism 84 is placed in an opened state when the forward-backward slide base 100 is located at the backward end. When the forward-backward slide base 100 is located at the forward end, the shutter mechanism 84 is in a closed state as illustrated in FIG. 5.

The operation panel 18 includes a panel frame 118 having the bottom wall 119. The panel frame 118 includes a handle portion 118A on the front side thereof and also has a hollow interior. An opening portion 119A is formed in the bottom wall 119 slightly toward the backward side with respect to the center thereof. The rotor 114 is attached to the opening portion 119A, and the non-rotational gear 116 protrudes into the panel frame 118 via the opening portion 119A.

The base 20 includes a rear end portion 20A in which an opening portion 20E for mounting the pivot mechanism and for passing a cable therethrough is formed. A passage 20F serving as a slot is formed continuously to the opening portion 20E, so as to allow a cable to be externally inserted into the rear end portion after the movable section is set onto the main unit.

In the hollow portion of the handle portion 118A, a release lever 124 is disposed, and also cables 126 and 128 are also disposed as required. The release lever 124 is operated for releasing a lock state when the operation of the left-right slide mechanism 62 and the forward-backward slide mechanism 64 is in a stop state; i.e. in a lock state, in the present embodiment. The lock state is attained by holding the shaft member with a fixed force, and at this time, the lock state is attained by increasing the frictional resistance. A brake mechanism 120 is placed on the bottom wall 119 of the panel frame 118, and engages the non-rotational gear 116 to exert a constant braking force with the rotation movement of the operation panel 18. As the frictional resistance of the brake mechanism 120 is relatively large, the operation panel 18 is prevented from performing rotation movement by itself, even if an external force acts on the display unit to move the arm mechanism. The cable 122 performs a locking operation when the brake mechanism 120 functions as a lock mechanism.

Figure 6:
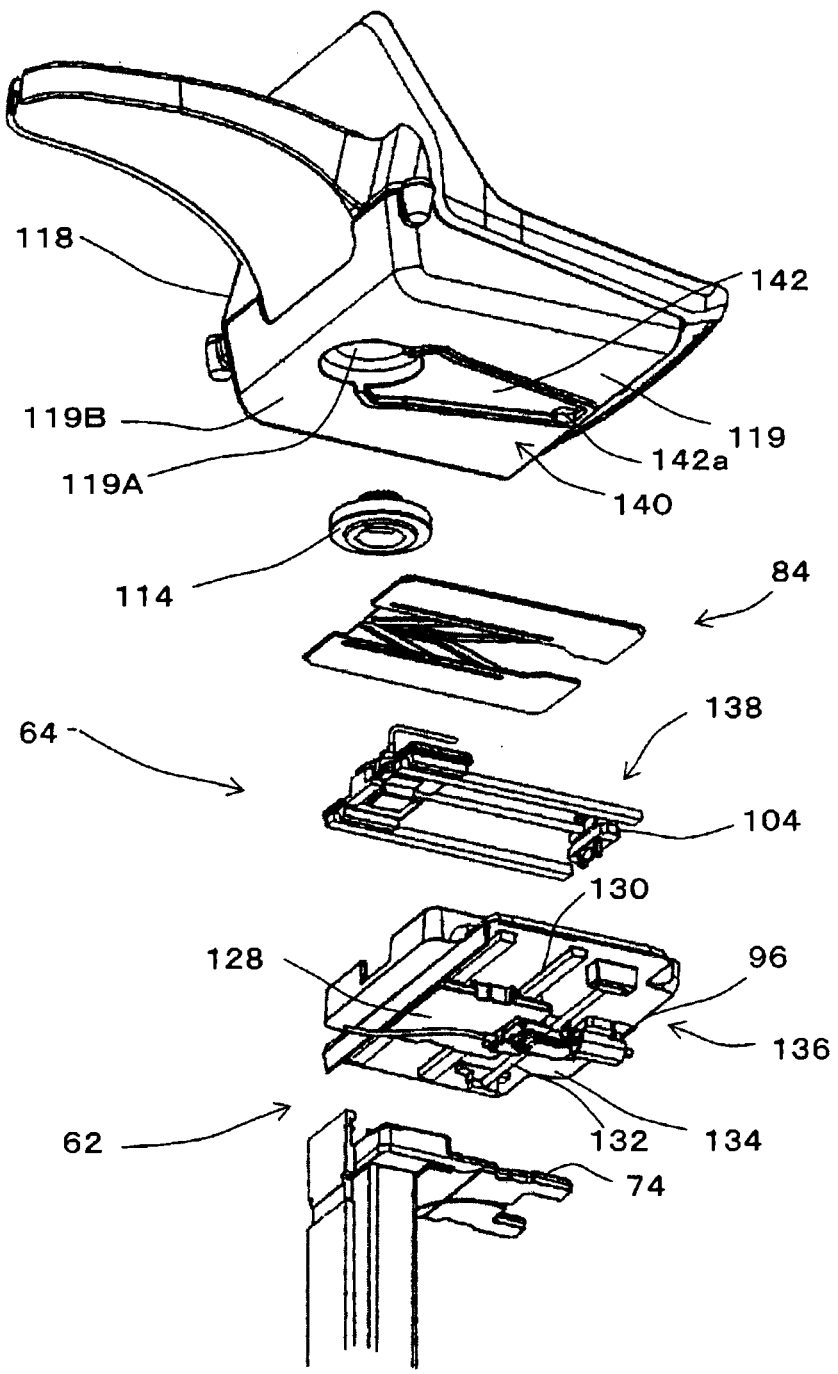
FIG. 6 Second exploded perspective view illustrating the movable mechanism as viewed obliquely from below.

FIG. 6 illustrates an exploded perspective view of the movable mechanism as viewed obliquely from below. As has been already described, from bottom to top, the left-right slide mechanism, the forward-backward slide mechanism, the rotation mechanism, and the operation panel are stacked. The left-right slide mechanism 62 will be described. The left-right slide base 96 is a horizontal plate, and a pair of left-right slide rails 130, which are members extending in the left-right direction, are provided on the lower surface side thereof. A guide shaft 132 is attached to the left-right slide base 96. Reference numeral 134 indicates a left-right slide lock mechanism, which holds the guide shaft 132 to thereby lock the slide movement in the left-right direction. Further, reference numeral 136 indicates a home position lock mechanism, which will be described below. Reference numeral 128 indicates a rail stand which is fixed to the movable base 74. The left-right slide base 96 moves freely in the left-right direction on the rail stand 128. On the left-right slide base 96, the rotation mechanism moves freely in a sliding manner in the forward-backward direction by means of the forward-backward slide mechanism 64.

On the bottom wall 119 of the operation panel, a frame body 140 projecting downward from the lower surface side thereof is formed. Specifically, the frame body 140 is formed on the bottom surface 119B. The frame body 140 defines a movement region 142 for receiving a projecting portion pair 138 serving as a moving element and allowing the projecting portion pair 138 to move therein. The frame body 140 and the moving elements 138 serving as the projecting portion pair constitute a rotation limitation mechanism. The rotation limitation mechanism is a mechanism that variably sets the rotatable angle range in accordance with the sliding position of the operation panel in the forward-backward direction. In the present embodiment, the rotatable angle range is set to zero when the operation panel is located at the backward end, and the rotatable angle range gradually increases towards the forward end. In order to define such a change, the frame body 140 has a left-right width that gradually widens from the front side toward the rear side thereof. Here, FIG. 6 also illustrates the shutter mechanism 84 in its closed position. When the forward-backward slide base is located at the backward end on the forward-backward slide mechanism 64, the shutter mechanism 84 is in an opened state as described above. The bottom wall 119 includes the opening portion 119A formed therein, into which a portion of the rotor 114 is inserted.

Next, with reference to FIGS. 7 to 11, each of the mechanisms described above will be individually described.

Figure 7:
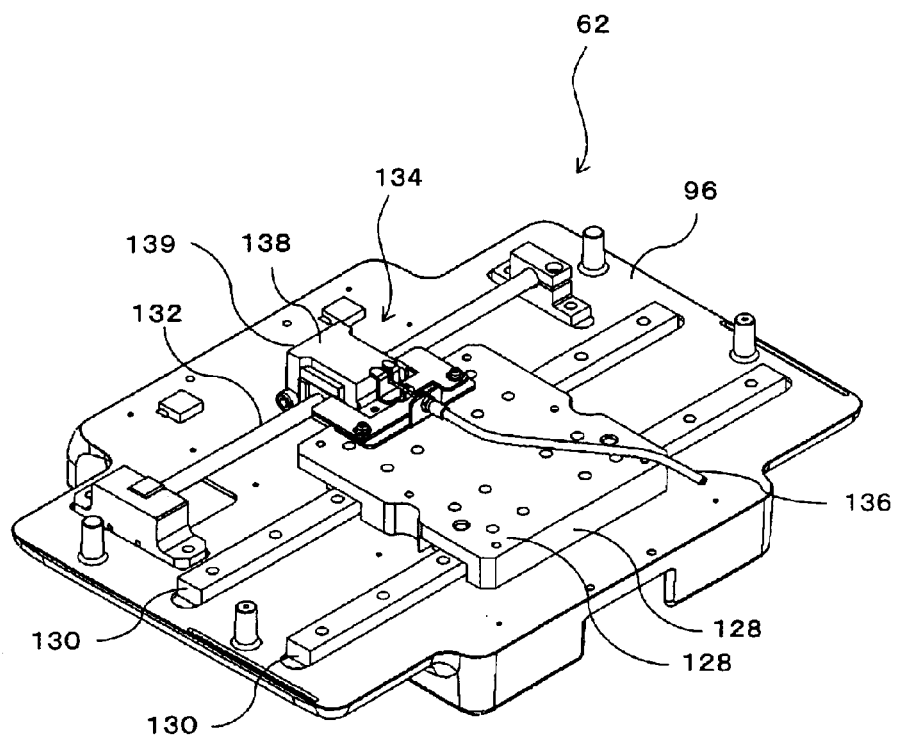
FIG. 7 Perspective view illustrating a left-right slide mechanism which is inverted.

FIG. 7 illustrates the left-right slide mechanism 62, although the left-right slide base 96 is illustrated as being inverted. On the lower surface side of the left-right slide base 96, the pair of left-right slide rails 130 is provided as described above. The pair of left-right slide rails 130 are provided at a fixed interval in the front-rear direction. The pair of slide rails 130 engage the rail stand 128 such that the left-right slide base 96 is movable with respect to the rail stand 128 in the left-right direction. The left-right slide lock mechanism 134 is mounted on the rail stand 128. The left-right slide lock mechanism 134 is a mechanism that locks the slide movement in the left-right direction by holding the guide shaft 132. The operation force of the left-right slide lock mechanism 134 is applied by a cable 136, a spring, or the like. Actually, a release force is applied by the cable 136. The left-right slide lock mechanism 134 includes a slide block 138 for holding the guide shaft 132, and the slide block 138 includes, on the front surface side thereof, an engagement surface 139. The engagement surface 139 has an engagement hole that receives a horizontal pin provided in the home position lock mechanism. The surfaces on the right and left sides of the engagement hole are slanted.

Figure 8:
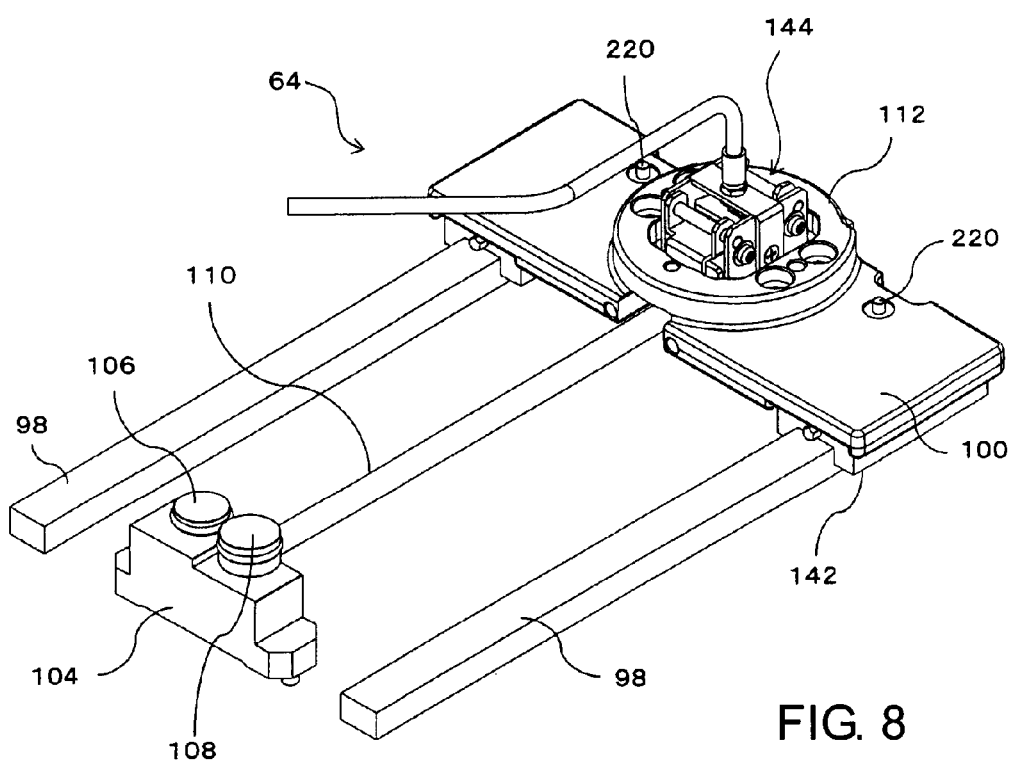
FIG. 8 Perspective view illustrating a forward-backward slide mechanism.
Figure 9:
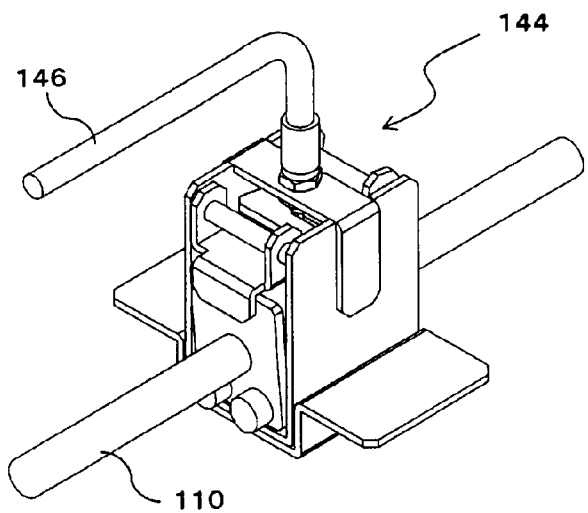
FIG. 9 Perspective view illustrating a mechanism which locks the forward-backward sliding motion.

FIG. 8 illustrates the forward-backward slide mechanism 64. The forward-backward slide mechanism 64 includes a pair of forward-backward slide rails 98 which are provided in the left-right direction at a fixed distance. The forward-backward slide mechanism 64 further includes a guide shaft 110. A block 104, which is provided on the front end side of the guide shaft 110, is fixed to the left-right slide base. On the forward-backward slide rails 98, the forward-backward slide base 100, which is movable in the forward-backward direction, is mounted via a pair of sliders 142. The non-rotational base 112 is mounted on the forward-backward base 100. The non-rotational base 112 includes a hollow portion formed in the center portion, in which the forward-backward slide lock mechanism 144 is disposed. As illustrated in FIG. 9, the forward-backward slide lock mechanism 144 is a mechanism that locks a slide movement in the forward-backward direction by holding the guide shaft 110. The cable 146 or a spring mechanism is provided for applying such an operation force. More specifically, the cable 146 transmits a release force.

Referring back to FIG. 8, on the forward-backward slide base 100, a pair of slide pins 220 are formed at a fixed distance in the left-right direction so as to project therefrom. Each slide pin 220, which is a member projecting upward, constitutes an important element of the shutter mechanism. Specifically, when the forward-backward slide base 100 moves in the forward-backward direction, the pair of slide pins 220 also move in the forward-backward direction accordingly, such that the pair of slide pins 220 operate in accordance with the sliding position in the forward-backward direction to thereby determine the degree of opening of the shutter plate, as will be described below.

Figure 10:
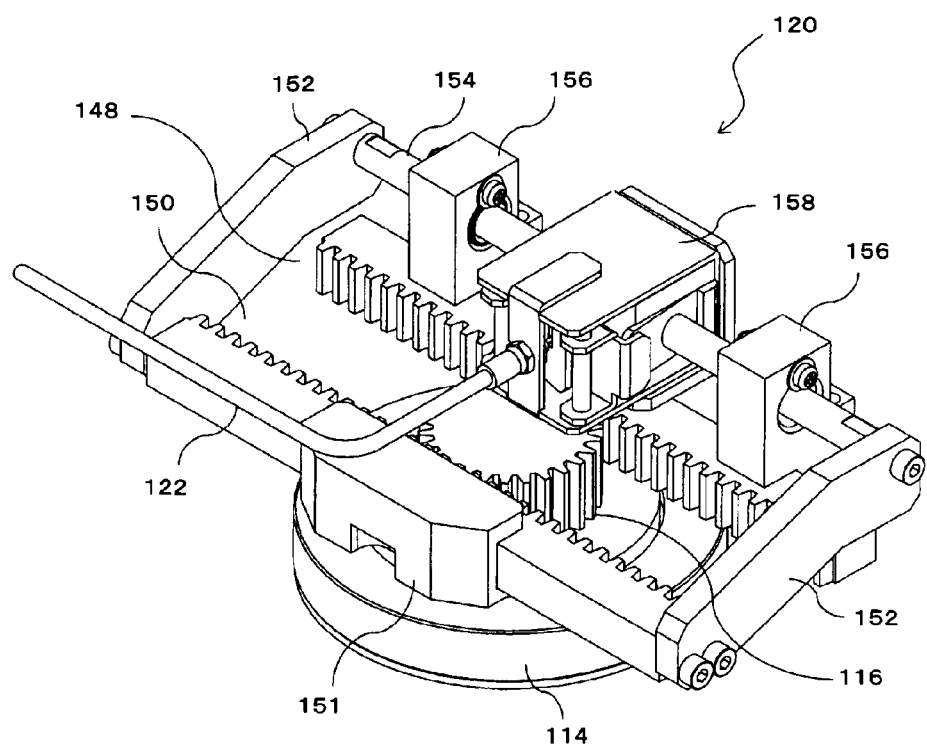
FIG. 10 Perspective view illustrating a brake mechanism which provides sliding resistance during a rotating motion.

FIG. 10 illustrates an example of the brake mechanism 120. The rotor 114 is coupled to the bottom wall in a fixed manner. As such, the operation panel can rotate freely with the rotor 114. A pair of racks; i.e. a first rack 148 and a second rack 150, engage with the non-rotational gear 116. The second rack 150 is held by the block 151 such that the second rack 150 can move in the axial direction. A guide shaft 154 is coupled to the second rack 150 via a pair of arm members 152, and a pair of sliders 156 are provided on the guide shaft 154. The first rack 148 is fixed to these sliders 156. A grip portion 158 is provided at the center portion of the guide shaft 154 and is fixed to the first rack 148.

When the operation panel rotates, the first rack 148 and the second rack 150 that are engaged with the non-rotational gear 116 move in a sliding manner in opposite directions. In this case, the guide shaft 154 also moves in a sliding manner with respect to the grip portion 158. By exerting a predetermined brake force on the grip portion 158, the sliding movement of the guide shaft 154 is restricted; specifically, the brake force acts on the rotation movement of the operation panel. Although the cable 122 is used to control the operation of the grip portion 158, this cable 122 is not necessary if the brake force is continuously exerted on the grip portion 158. Further, a single rack may be provided, rather than two racks.

Figure 11:
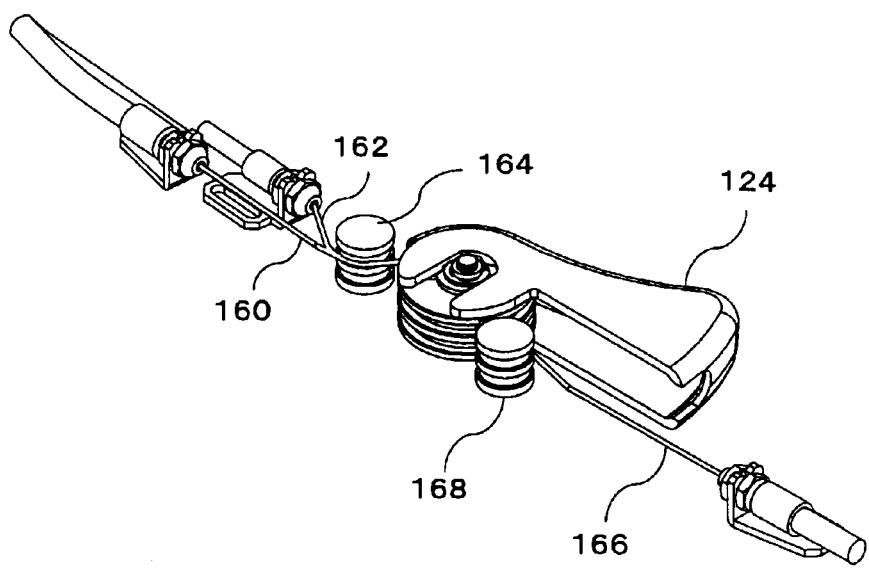
FIG. 11 View for explaining a change in the range of a rotatable angle in accordance with a forward and backward sliding position.

FIG. 11 illustrates the release lever 124. The release lever 124 is a member which is operated by a user to release (an unlock operation) the plurality of lock mechanisms collectively. Specifically, wires 160 and 162 are wound around the rotational shaft of the release lever 124 via a guide 164, and a wire 166 is similarly wound around the rotational shaft of the release lever 124 via a guide 168. Accordingly, by holding the release lever 124, it is possible to place the three lock mechanisms into a released state simultaneously. In the present embodiment, however, as a brake force continuously acts on the rotation mechanism, the release mechanism actually functions only on the left-right slide mechanism and the forward-backward slide mechanism. More specifically, only two wires are actually wound around the rotational shaft of the release lever 124. As a matter of course, the release lever 124 can be operated to perform a lock operation. In any case, such a structure, in which it is possible to achieve a plurality of lock (unlock) operations by a single action, is simple and can provide good operability.

Figure 12:
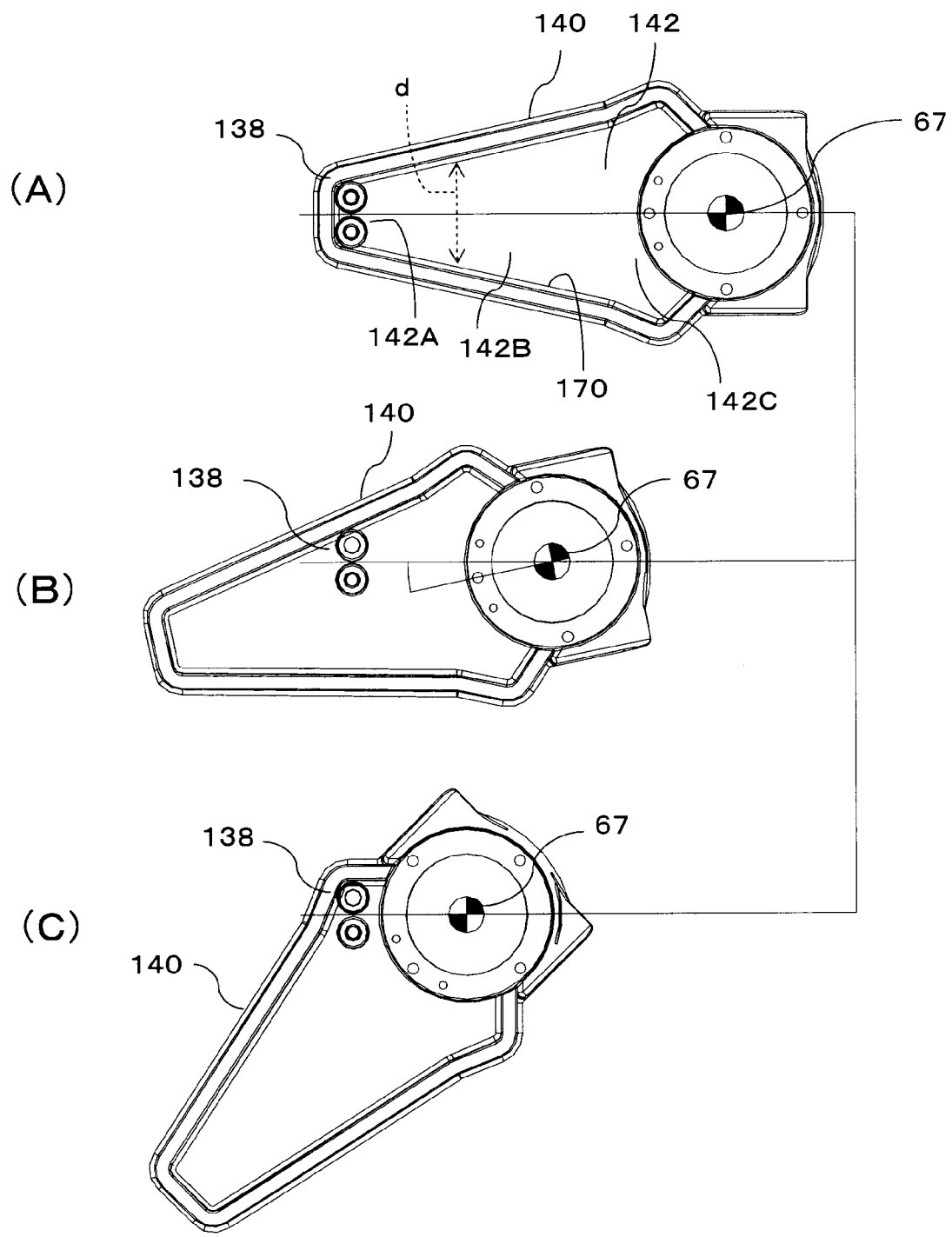
FIG. 12 View illustrating operation examples of a rotation limit mechanism.

FIG. 12 illustrates an operation of the rotation limitation mechanism. FIG. 12(A) illustrates a state in which the operation panel is at the backward end; FIG. 12(B) illustrates a state in which the operation panel is at the center position in the forward-backward direction; and FIG. 12(C) illustrates a state in which the operation panel is at the forward end. In FIG. 12, the left side corresponds to the front side of the operation panel and the right side corresponds to the rear side of the operation panel. Reference numeral 67 indicates a rotation center axis.

In FIG. 12(A), the frame body 140 defines a movement region 142 of a moving element 138. More specifically, the frame body 140 is formed by a regulation wall 170. In the movement region 142, the width d in the left-right direction gradually increases from the front side toward the rear side. Reference numeral 142A indicates a front side position, reference numeral 142B indicates an intermediate position, and a reference numeral 142C indicates a rear side position. In FIG. 12(A), the moving element 138 is positioned at the forward end of the movement region 142, and is not in a state in which the movement element can move in the left-right direction. At such a home position, the rotational movement of the operation panel is inhibited. In other words, the rotatable angle range is zero. As such, because the rotational movement of the operation panel is restricted when the operation panel is at the backward end, it is possible to avoid the problem that the movable section collides with the main unit.

In FIG. 12(B), the moving element 138 is at the intermediate position; i.e., the operation panel is drawn toward the front side to the intermediate position. In such a state, the moving element 138 can move over a predetermined range in the left-right direction; more specifically, can move along an arc. In FIG. 12(C), the operation panel is drawn to the forward end, and in this state, the moving element 138 can move maximally in the left-right direction; more specifically, in the arc direction, and a large rotatable angle range is set.

As described above, with the rotation limitation mechanism, it is possible to adaptively set the rotatable angle range in accordance with the sliding position of the operation panel in the forward-backward direction. Accordingly, there can be obtained the advantage that the angle range which is appropriate for the sliding position can be set while avoiding collision between the movable section and the main unit. In particular, as a very large rotation is permitted when the operation panel is located at the forward end or near the forward end, the advantage of significantly improved usability can be achieved.

Figure 13:
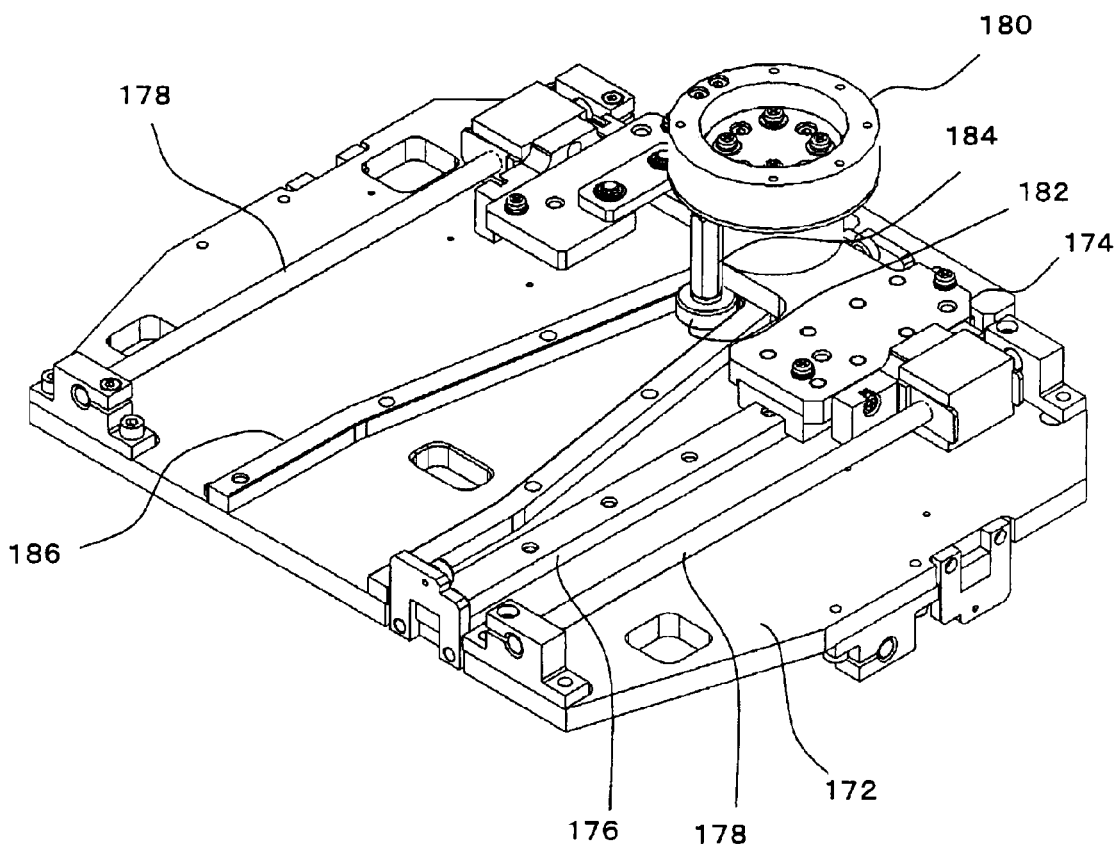
FIG. 13 Perspective view illustrating another embodiment of the rotation limit mechanism.

FIG. 13 illustrates another embodiment of the rotation limitation mechanism. On a left-right slide base 172, a single forward-backward slide rail 176 is provided, and two guide shafts 178 are provided via a predetermined member. On the forward-backward slide rail 176, a forward-backward slide base 174 is mounted. Further, a frame body 186 which defines a movement region of a contact element 182 is mounted on the left-right slide base 172. The width of the frame body 186 in the left-right direction is increased from the rear side toward the front side. Specifically, the change of size in the frame body 186 is opposite that of the frame body illustrated in FIG. 12.

The contact element 182 described above is mounted on a rotator; i.e., a rotation base 180, via a coupling shaft 184. FIG. 13 illustrates a state in which the operation panel is located at the backward end, in which state the contact element 182 is located at the rearmost position, and the movement of the contact element 182 in the left-right direction is completely restricted by the frame body 186. In other words, at such a home position, the rotation movement of the operation panel is inhibited. With the sliding movement of the operation panel in the forward direction, movement of the contact element 182 in the left-right direction is permitted. Specifically, the rotation of the operation panel is allowed in accordance with the left-right width of the frame body 186.

Figure 14:
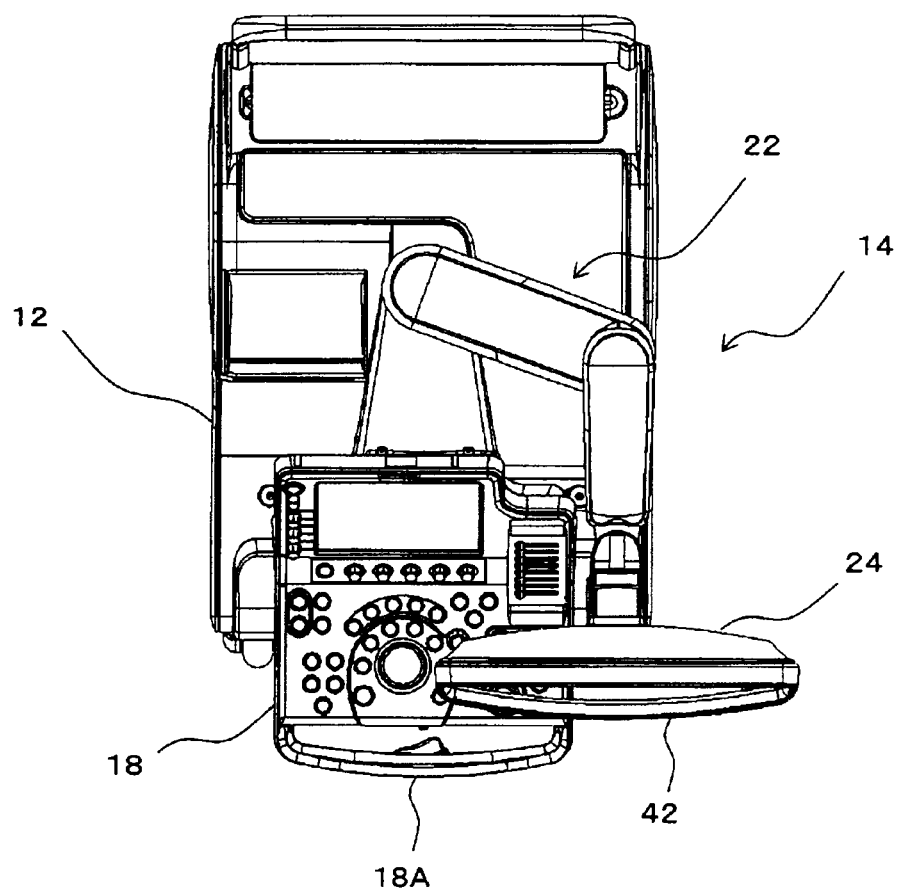
FIG. 14 Top view illustrating a first example state of an operation panel and a display unit.
Figure 15:
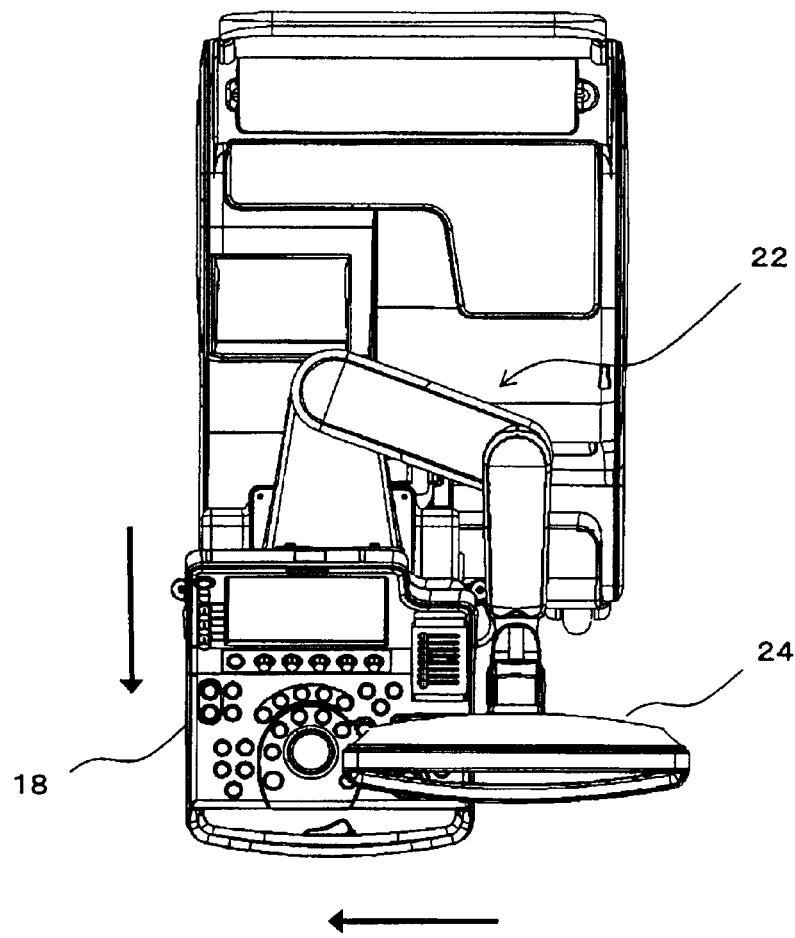
FIG. 15 Top view illustrating a second example state of an operation panel and a display unit.
Figure 16:
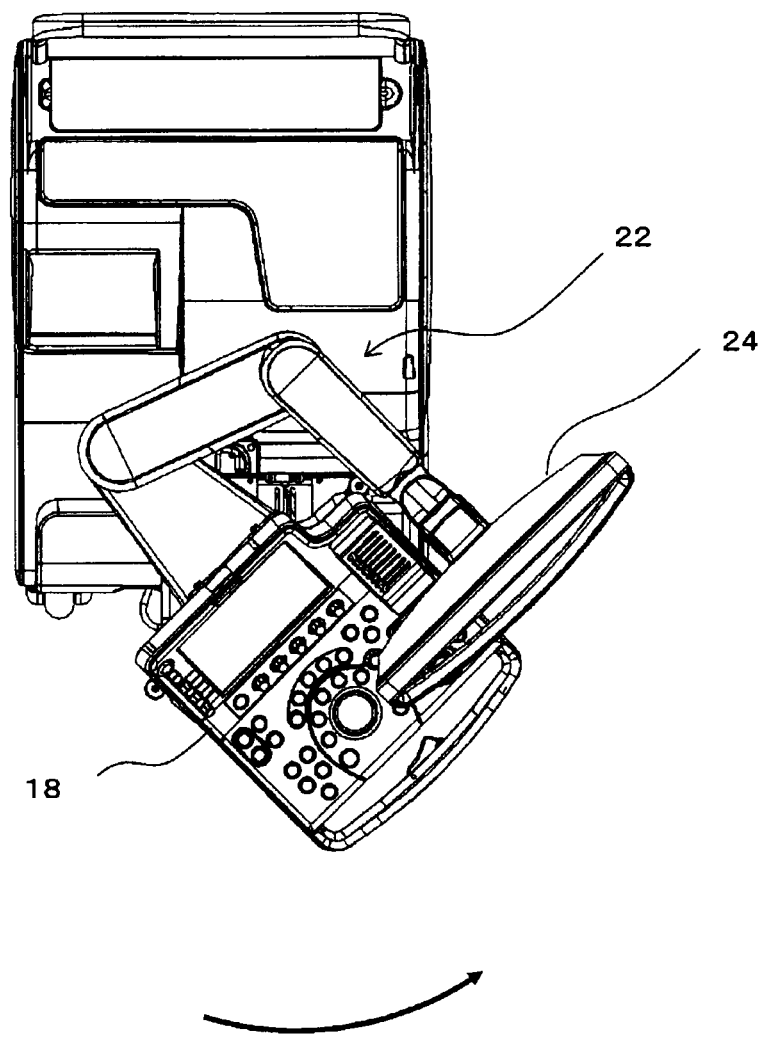
FIG. 16 Top view illustrating a third example state of an operation panel and a display unit.

(3) Setting Examples (FIGS. 14 to 16)

Next, various setting examples will be described with reference to FIGS. 14 to 16. Referring to FIG. 14, the handle 18A is provided on the front side of the operation panel 18. The user can move the movable section 14 while holding the handle 18A, thereby setting the position and attitude of the operation panel 18 as desired. Further, the handle 42 is provided on the display unit 24, and the display unit 24 can be set to a desired position and attitude by moving the display unit 24 while holding the handle 42. As described above, the movable mechanism which supports the movable section 14 is normally in a locked state or in a state in which a friction is exerted, and the arm mechanism is also in such a locked state. However, because, in the present embodiment, the brake force in the movable mechanism is set to be always greater than the brake force in the arm mechanism, it is possible to prevent the movable section 14 from moving by itself when the display unit 24 is moved.

In FIG. 14, the operation panel 18 is located at the center position in the left-right direction and at the backward end in the forward-backward direction. The pivot angle of the operation panel in this state is set to 0 degrees. In other words, the operation panel 18 is located at the home position. Meanwhile, due to the action of the arm mechanism 22, the display unit 24 is drawn to the position above the operation panel 18.

FIG. 15 illustrates a state in which the movable section is slid to the left direction from the state illustrated in FIG. 14. Further, FIG. 16 illustrates a state in which the operation panel 18 is further drawn in the forward direction and to the right direction from the state of the operation panel 18 as illustrated in FIG. 14 and is then further pivoted counterclockwise. In another example, by positioning the operation panel at the right end and forward end and then pivoting the operation panel 18 clockwise, even when a user, who is located a certain distance from the main unit, takes a slanted posture with respect to the main unit, it is possible to position the operation panel right in front of the user and further direct the operation panel toward the user. Also, in the present embodiment, it is possible to move the display unit in back of the main unit and further direct the display unit toward the rear side. It is also possible to locate the display unit to the right side of the main unit and then lower and position the display unit near the head of the user lying in a bed. As such, in the present embodiment, as the base extends in the depth direction and the arms in the arm mechanism have a certain degree of length, the movable region of the display unit 24 is significantly large.

Figure 17:
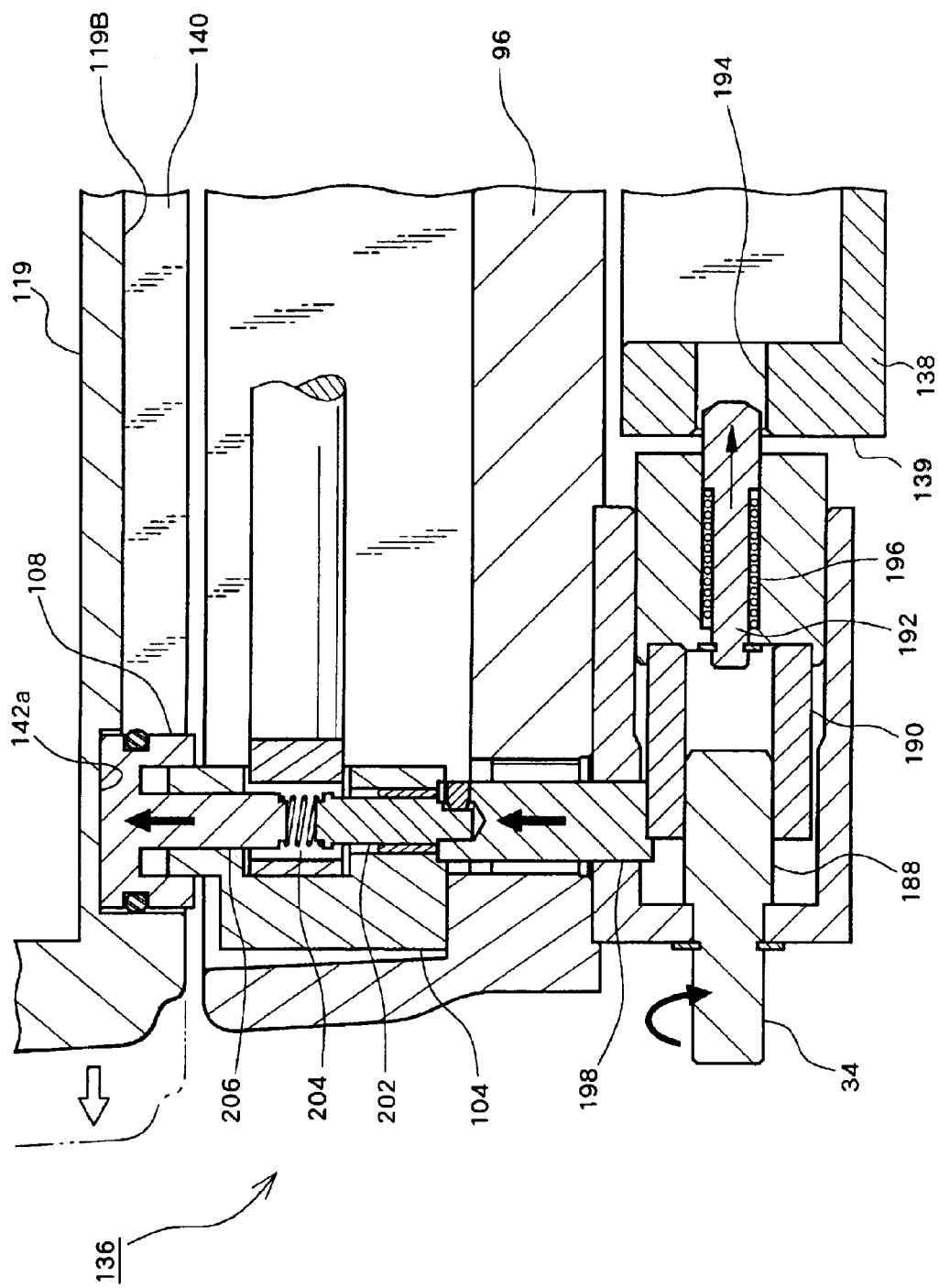
FIG. 17 Cross sectional view illustrating a home position lock mechanism.

(4) Home Position Lock Mechanism (FIG. 17)

With reference to FIG. 17, the home position lock mechanism 136 will be described. The home position lock mechanism 136 is a mechanism which inhibits the slide movement in both the left-right direction and the forward-backward direction when the operation panel; i.e., the movable section, is at a home position. In this state, the operation panel is prohibited from moving by merely gripping the release lever 124.

The knob 34 is connected to a shaft 188, and with the rotation of the knob 34, the shaft 188 rotates, which further causes a cam member 190 to rotate. Here, the cam member 190 and the peripheral structure thereof are illustrated in a simplified manner. With the action of the cam member 190, a horizontal pin 192 is driven forward. The horizontal pin 192 is urged forward by a spring 196. Stated conversely, the horizontal pin 192 is capable of retreating movement over a predetermined distance.

On the movable base, the slide block 138 is provided. The slide block 138 has, as a front surface, an engagement surface 139 having an engagement hole 194. The right and left sides of the engagement hole 194 are formed as slope surfaces. Accordingly, if, in a state in which the horizontal pin 192 projects, the left-right slide base 96 moves horizontally to reach the center position, the leading end portion of the horizontal pin 192 ascends the slope surface formed on the engagement surface 139 and finally comes into the engagement hole 194. In this state, the movement of the left-right slide base 96 in the left-right direction is prohibited; i.e., the left-right slide base 96 is placed into a locked state in the left-right direction.

On the other hand, with the rotation movement of the shaft 188, a member 198 extending in the vertical direction is thrust upward to thereby thrust a first vertical pin 202 and a second vertical pin 206 upward. However, a spring 204 is interposed between the first vertical pin 202 and the second vertical pin 206, and the second vertical pin 206 is urged upward with respect to the first vertical pin 202. As such, a structure which extends through a block 104 in the up-down direction is formed in the block 104, and the thrust-up force of the first vertical pin 202 is applied to the second vertical pin 206 via the spring 204. The upper portion of the second vertical pin 206 is formed as a thrust portion 108, which is a roller. As described above, the frame body 140 defines a movement space of the thrust portion 108 and includes a recess portion 142a formed at a position corresponding to the home position. The recess portion 142a is a hollow and therefore has a shape which is retracted upward with respect to the bottom surface 119B. Accordingly, when the knob 34 is operated, an upward urging force is continuously applied to the thrust portion 108, so that the thrust portion 108 moves horizontally while remaining in contact with the bottom surface 119B. Then, when the thrust portion 108 is fitted into the recess portion 142a, the horizontal movement of the thrust portion 108 is inhibited; specifically, the bottom wall 119 is fixed with respect to the left-right slide base 96. In this state, the slide movement in the forward-backward direction and the rotation movement are inhibited. As such, it is possible to lock the left-right movement, the forward-backward movement, and also the rotation movement by simply operating the knob 34. In addition, the operation of the knob 34 can be performed at positions other than the center position or the forward end position, and when the center position is achieved in the slide movement, a lock state is automatically formed, and also when the rotation angle becomes 0 degrees at the backward end position, a lock state in the forward-backward direction and the rotation direction can be automatically formed. In the present embodiment, by using the layered relationship to exert an acting force through a plurality of layers as described above, the integral lock mechanism can be achieved.

(5) Shutter Mechanism (FIGS. 18 to 22)

Figure 18:
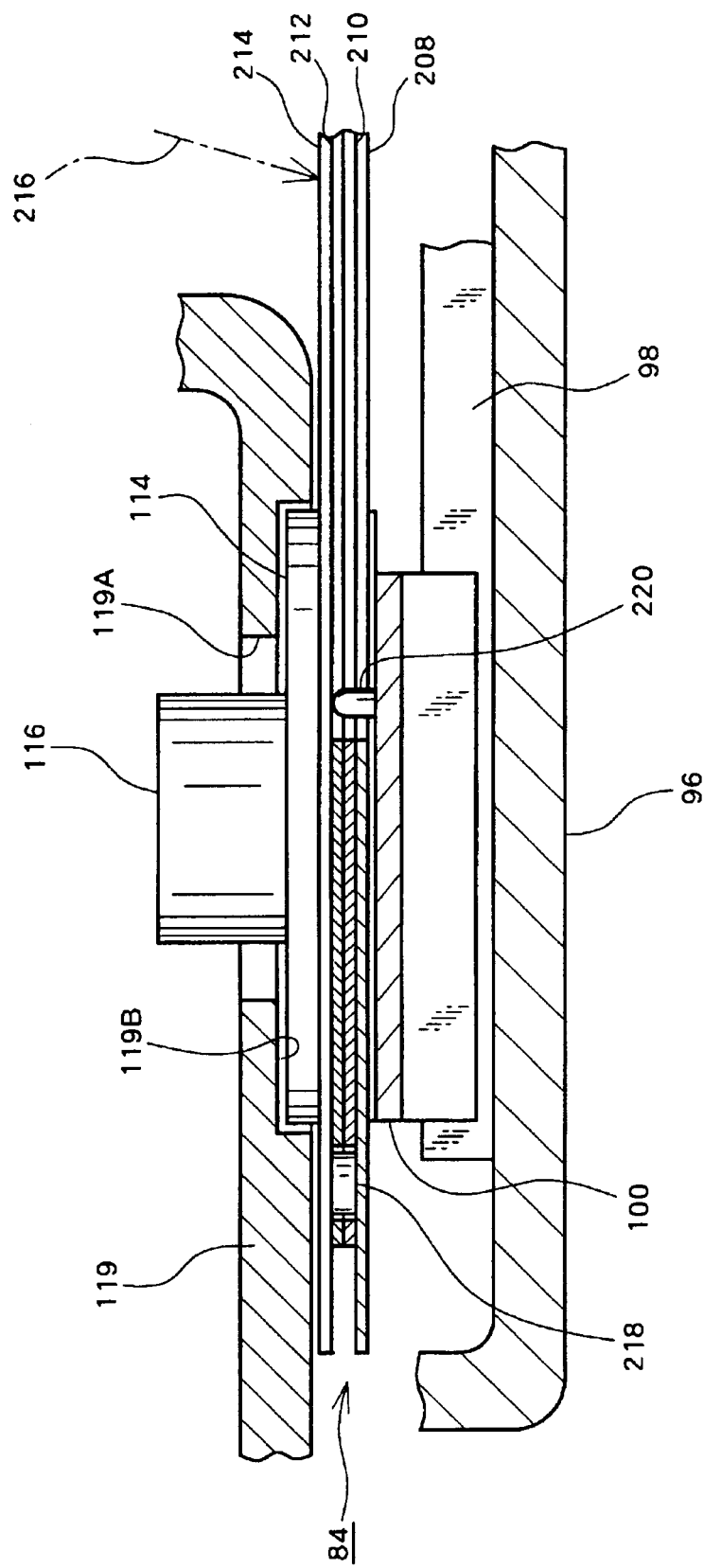
FIG. 18 Cross sectional view illustrating a shutter mechanism.

Next, with reference to FIGS. 18 to 22 the shutter mechanism will be described in detail. Referring to FIG. 18, the pair of forward-backward slide rails 98 are provided on the left-right slide base 96, and the forward-backward slide base 100 is mounted on these forward-backward slide rails 98. In FIG. 18, the forward-backward slide base 100 is at the forward end. On the forward-backward slide base 100, the rotor 114 is rotatably mounted, and the non-rotational gear 116 is further provided. The rotor 114 is fitted into an annular base 119B formed in the bottom wall 119, and is integrated with the bottom wall 119 in such a fitted state. The non-rotational gear 116 enters the panel frame via the opening portion 119A. Only a slight gap is present between the forward-backward slide base 100 and the bottom wall 119, and in the present embodiment, the shutter mechanism 84 is disposed in such a gap. The shutter mechanism 84 may be coupled with the left-right slide base 96 or placed within the center case. The shutter mechanism 84 includes a pair of lower plates 208, a pair of first shutter plates 210, a pair of second shutter plates 212, and a pair of upper plates 214. Each of the plates 208, 210, 212, and 214 is a thin sheet-like member which is formed of a resin having a black color, for example. Each plate is desirably formed of an opaque member.

On the pair of lower plates 208, a pair of rotational shafts 218 are spaced at an interval in the left-right direction. Each rotational shaft 218 functions as a rotational shaft for the respective first shutter plate 210 and second shutter plate 212. The pair of rotational shafts 218 and the pair of upper plates 214 may be coupled in a fixed manner. Each of the pair of lower plates 208, the pair of first shutter plates 210, and the pair of second shutter plates 212 has a single pin slot formed therein as will be described below, and a slide pin 220 is inserted in each pin slot. A pair of slide pins 220 are provided at a distance in the left-right direction on the forward-backward slide base 100, and perform a slide movement with the forward-backward slide movement of the forward-backward slide base 100. Meanwhile, the pair of rotational shafts 218 do not slide in the forward-backward direction, although the pair of rotational shafts 218 slide in the left-right direction with the movement of the slide base 96. As indicated by reference numeral 216, the opening in the upper portion of the main case serves as a movement space for the rotor 114; specifically, an exposed opening portion is uncovered on the rear side of the operation panel, and this leads to a problem that the internal mechanisms are exposed through such an opening portion as indicated by reference numeral 216. The shutter mechanism is a mechanism which conceals such an opening portion with the slide movement of the operation panel in the forward-backward direction.

Figure 19:
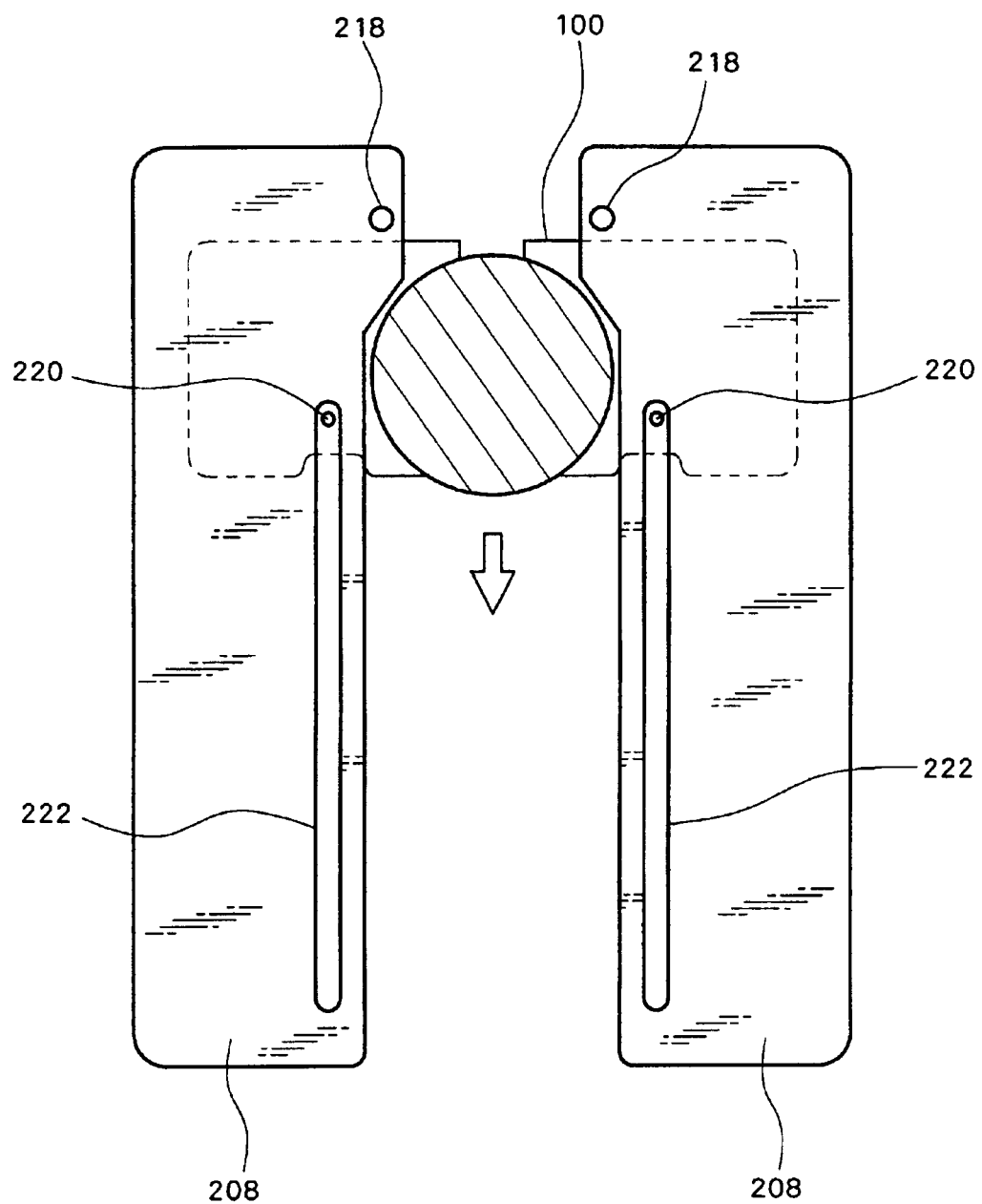
FIG. 19 Cross sectional view illustrating a lower part structure of the shutter mechanism.

FIG. 19 illustrates the pair of lower plates 208. In FIG. 19, the upper side corresponds to the front direction of the operation panel and the lower side corresponds to the rear side of the operation panel. In FIG. 19, the forward-backward slide base 100 is at the forward end. Each lower plate 208 includes a linear pin slot 222. The pair of slide pins 220 spaced in the left-right direction are provided on the forward-backward slide base 100. In addition, a pair of rotational shafts 218 are provided as fixed shafts.

Figure 20:
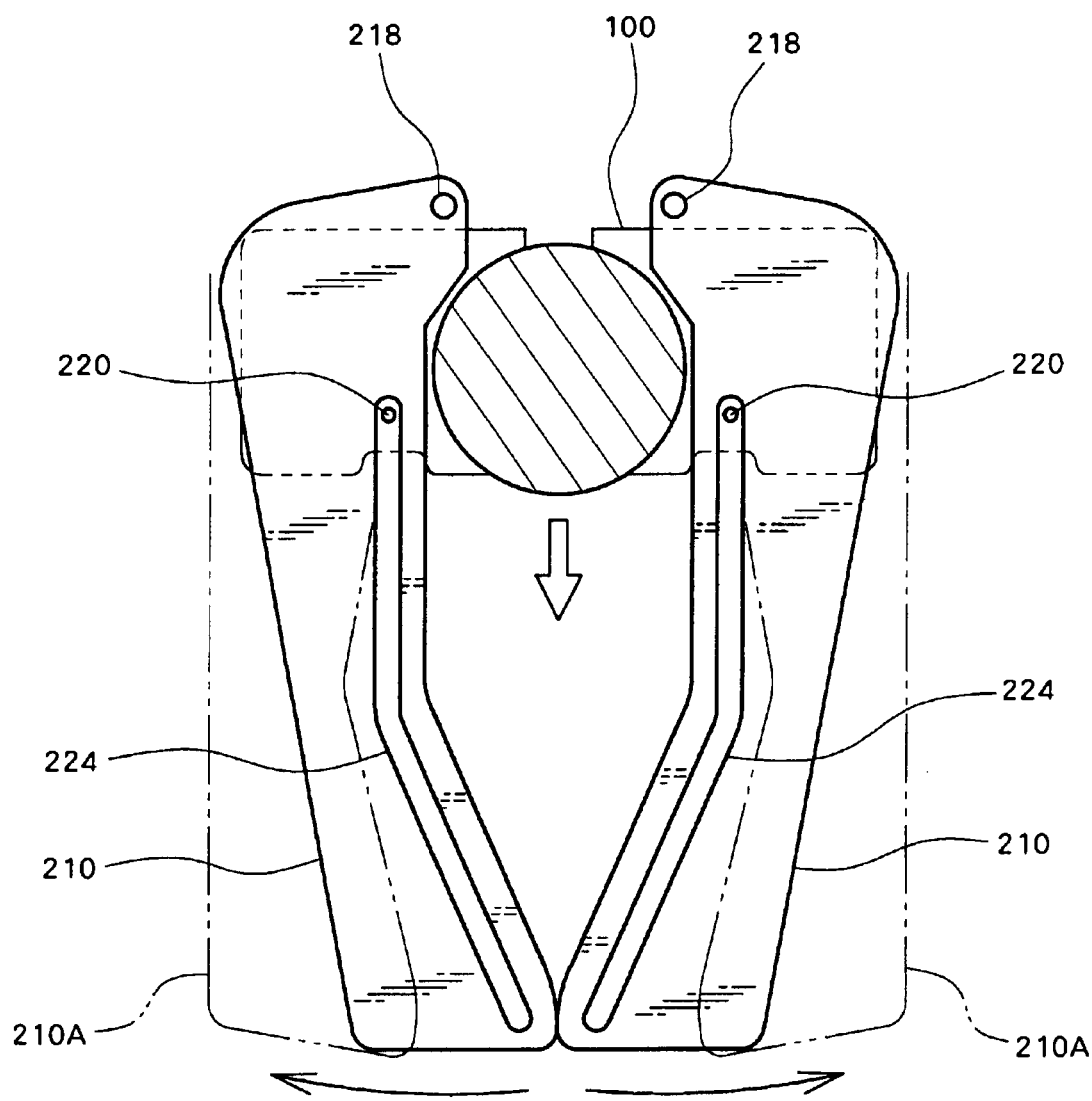
FIG. 20 Cross sectional view illustrating an intermediate part structure of the shutter mechanism.

FIG. 20 illustrates a pair of the first shutter plates 210. Each first shutter plate 210 performs rotational movement about the rotational shaft 218. A pin slot 224 is formed in each of the first shutter plates 210. Each pin slot 224 has a bent shape including a linear portion and a portion directed inwardly therefrom as illustrated in FIG. 20. In FIG. 20, the pair of the first shutter plates 210 are in a closed state. The pair of first shutter plates 210 in an opened state are indicated by reference numeral 210A. The pair of first shutter plates 210 serve to conceal especially the back area in the exposed space portion.

Figure 21:
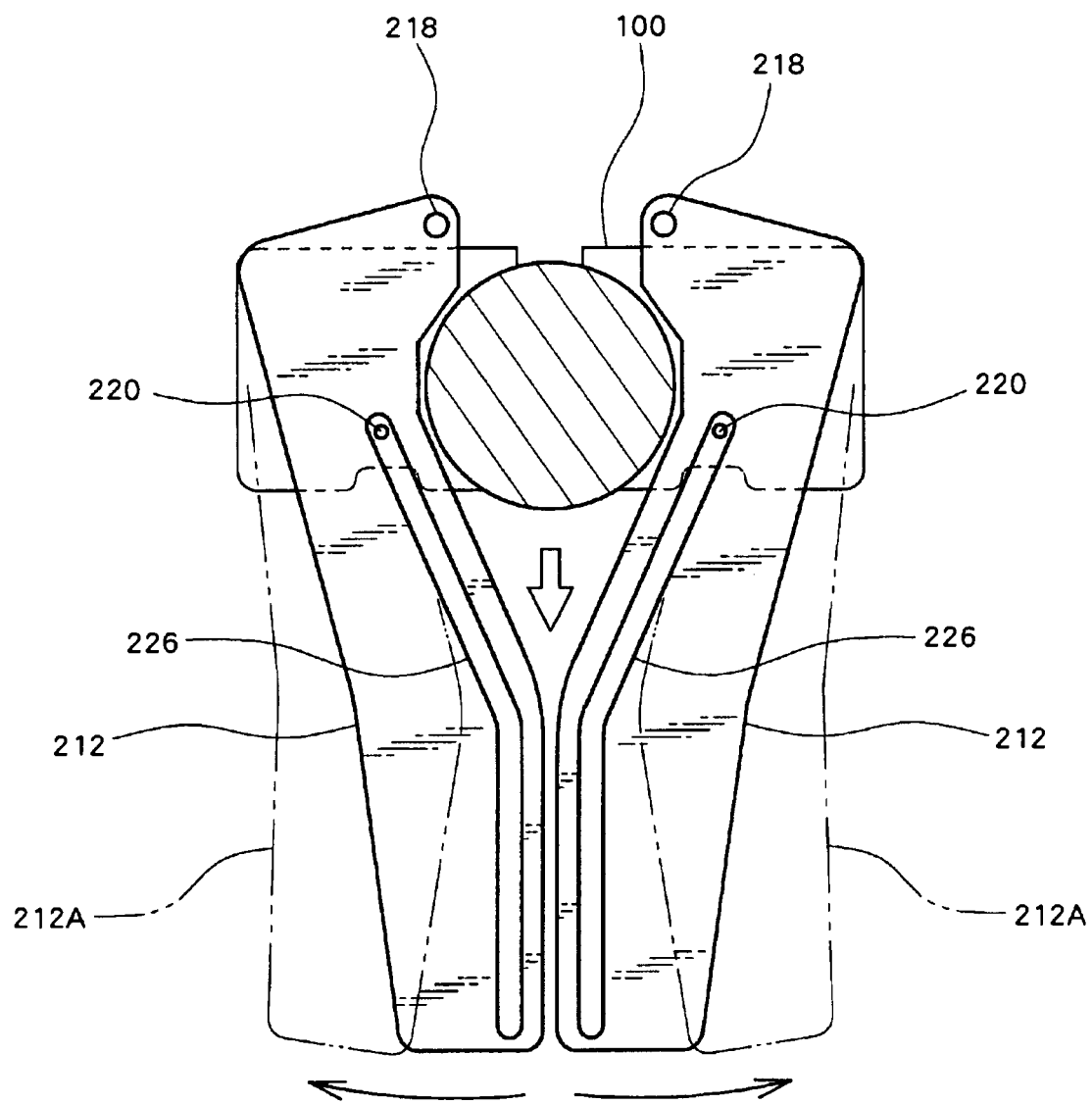
FIG. 21 Cross sectional view illustrating an upper part structure of the shutter mechanism.
Figure 22:
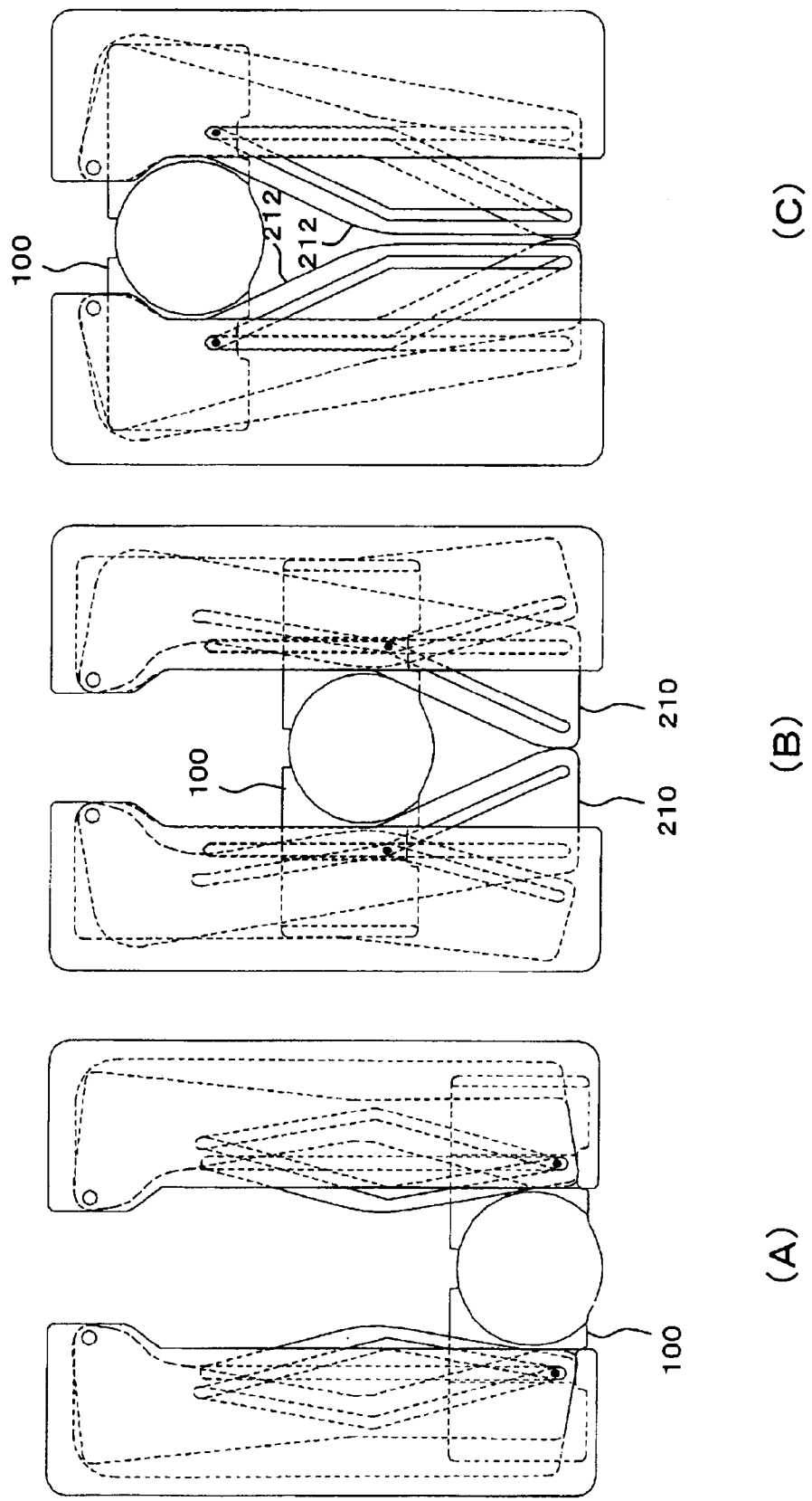
FIG. 22 View for explaining the operation of the shutter mechanism.

FIG. 21 illustrates a pair of second shutter plates 212. Each second shutter plate 212 performs a rotational movement about the rotational shaft 218. In the state illustrated in FIG. 21, a pin slot 226 is formed of an inwardly directed portion and a straight portion. In other words, the pin slot 226 has a bent shape. In FIG. 22, the pair of second shutter plates 212 are in a closed state. The pair of first shutter plates 212 in an opened state are indicated by reference numeral 212A. The pair of second shutter plates 212 serve to conceal the portion of the exposed opening portion from the intermediate area to the rear area.

Next, with reference to FIG. 22, the operation of the shutter mechanism will be described. FIG. 22(A) illustrates a state in which the forward-backward slide base 100 is at the backward end; FIG. 22(B) illustrates a state in which the forward-backward slide base 100 is at the intermediate position; and FIG. 22(C) illustrates a state in which the forward-backward slide base 100 is at the forward end. First, in the state illustrated in (A), all the shutter plates are in the opened state. Specifically, because the operation panel is located at the backward end and the opening portion is covered by the operation panel located above, the problem of exposure of the opening portion does not arise. Here, a passage of the rotational shaft member is formed between the two layered members provided on the left and right sides, and this passage forms the exposed opening portion at the rear portion of the moving rotational shaft member.

In FIG. 22(B), the operation panel is at the intermediate position, and in such a state, only the pair of first shutter plates 210 is placed in the closed state and the exposed opening portion formed on the rear side of the rotational shaft member is partially covered. In the state illustrated in FIG. 22(C), the operation panel is at the forward end, and a large exposed opening portion is formed on the back of the rotational shaft member. By placing the pair of second shutter plates 212 into the closed state, such an exposed opening portion is substantially covered. More specifically, when the operation panel moves from the backward end to the forward end, the pair of first shutter plates first start the closing movement, and subsequently the pair of second shutter plates start the closing movement. As such, by shifting the operation times for the two shutter plate pairs located at the upper and lower levels and also by allocating separate areas to be covered to these shutter plate pairs, even when a relatively large exposed opening portion is generated, such an opening portion can be concealed effectively and rapidly.

In the shutter mechanism described above, the pin slot is formed in each shutter plate, and the slide pin moves within the pin slot. The contact relationship between the pin slot and the slide pin changes depending on the lateral displacement of the pin slot; i.e., the shape of the pin slot, resulting in generation of a rotational force of the shutter plates. In the present embodiment, by employing the double shutter plates which are vertically layered and allowing these shutter plates to operate stepwise, and also by separating the areas covered by these shutter plates in the forward-backward direction, it is possible to conceal the exposed opening at an appropriate timing with the movement of the rotational shaft member and also to exert the concealing effect over the whole opening portion even if the opening portion to be concealed is large.

The pair of cover plates described above may be provided as required. Providing such a pair of cover plates can provide an advantage of enabling smooth movement of the shutter plates and also allowing physical protection of the shutter plates. In the present embodiment, because the two shutter plates are sandwiched by pairs of plates located above and below these shutter plates, it is possible to enable the two shutter plates to move smoothly in the horizontal direction. As the shutter mechanism of the present embodiment is configured to have the layered plate structure as described above, it is possible to reduce the overall thickness of the shutter mechanism to be significantly thin, which results in the advantage that the thickness of the horizontal movement mechanism can be reduced.

Figure 23:
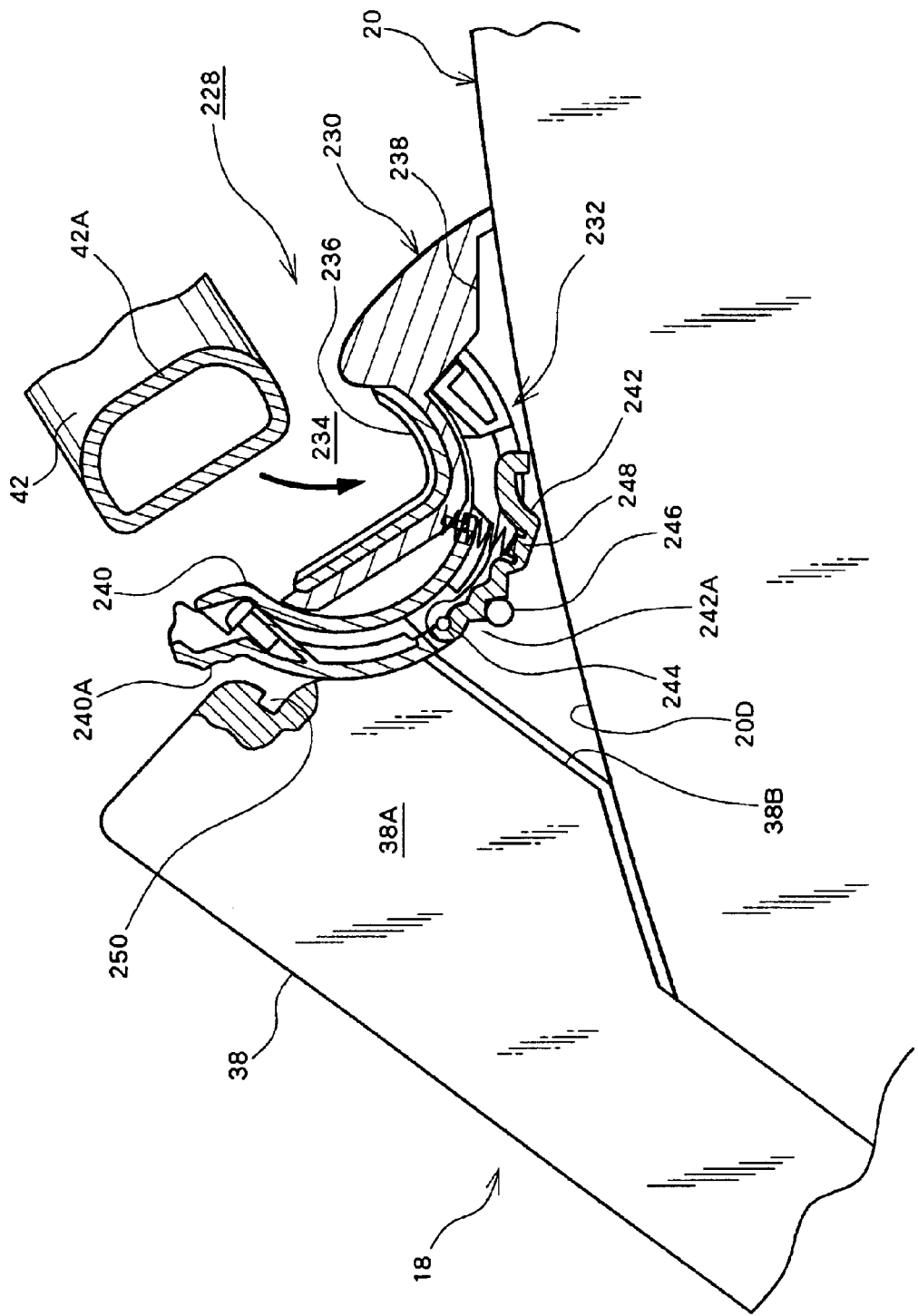
FIG. 23 Cross sectional view illustrating a state of a display unit restraint mechanism before being actuated.
Figure 24:
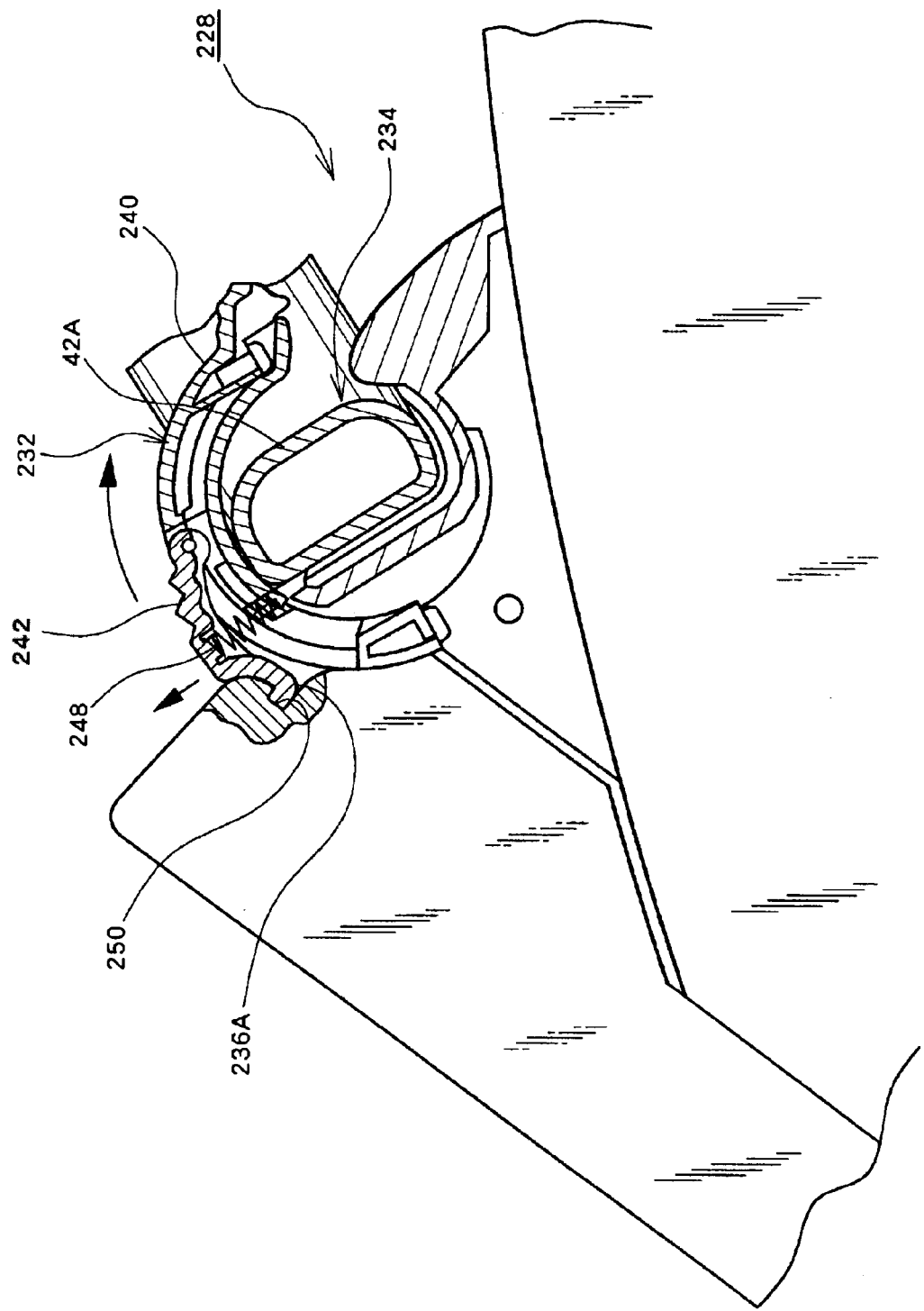
FIG. 24 Cross sectional view illustrating an actuated state of the display unit restraint mechanism.

(6) Display Unit Restraint Mechanism (FIGS. 23 and 24)

Next, with reference to FIGS. 23 and 24, the display unit restraint mechanism will be described. Referring to FIG. 23, the operation panel 18 includes the second operation section 38, the upper end portion 38A of which is illustrated in an enlarged view in FIG. 23. Meanwhile, the base 20 is coupled to the back surface side of the operation panel 18, and FIG. 23 illustrates the attachment end of the base 20. A display unit restraint mechanism 228 is provided in a gap having a triangular cross section which is sandwiched by the top face front end 20D of the base 20 and the back surface 38B of the upper end portion 38A.

The display unit restraint mechanism 228 is a mechanism which holds the handle 42 provided to the display unit to restrain the display unit itself during transportation of the device or the like. The display unit restraint mechanism 228 includes a fixed portion 230 and a rotation portion 232. The fixed portion 230 includes a catch member 236 forming a receiving groove 234. The catch member 236 has an opening which is opened toward the upward direction, which functions as a receiving port of the handle 42.

The rotation portion 232 is capable of rotational movement about a predetermined rotation center axis. The rotation portion 232 includes a cover portion 240 serving as a forward end on the rotation side. The surface of the cover portion 240 on the outer side is curved outward and bent, where a catching surface 240A is formed. By catching the catching surface 240A by finger tips to cause the cover portion 240 to move, it is possible to rotate the entire rotation portion 232.

The rotation portion 232 includes a hook member 242 which performs a rotation movement about a fixed axis 244. A spring 248 applies an urging force to the hook member 242 in a direction in which the hook member 242 rises up. The outer surface of the hook member 242 is a saw-toothed uneven surface 242A having projections and depressions, and a fixing pin 246 is in contact with the uneven surface 242A in the state illustrated in FIG. 23. As the urging force toward the outside acts on the hook member 242 by the spring 248, the fixing pin 246 fits into the depression of the uneven surface 242A, and, when the rotational section 232 is rotated, a consecutive click feeling can be obtained. Meanwhile, the upper end portion 38A includes a cut-out portion in which a hook slot 250 is formed. Further, the rotation portion 232 is held so as to prevent the rotation portion 232 from popping out of the position illustrated in FIG. 23 easily.

FIG. 23 illustrates an unactuated state of the display unit restraint mechanism 228. Meanwhile, FIG. 24 illustrates an actuated state of the display unit restraint mechanism 228. In FIG. 24, a handle main unit 42A fits into the receiving groove 234. The handle main unit 42A is a rod-like member extending in the horizontal direction. The cover portion 240 of the rotation portion 232 covers over the handle main unit 42A, so that the upward movement of the handle main unit 42A is restricted by the cover portion 240. Specifically, by cooperation of the fixed potion and the rotation portion 232, the handle main unit 42A is held firmly.

In a state in which the rotation portion 232 is rotated clockwise as illustrated in FIG. 24, the rising movement of the hook member 242 is permitted to thereby allow the leading end 236A thereof to be fitted into the hook slot 250. Specifically, in the housed state in which the rotation portion 232 is rotated counterclockwise, rise of the hook member 242 is inhibited by the pin or other structures, whereas by rotating the rotation portion 232 clockwise, a free movement of the hook member 242 is permitted so that the hook member 242 can rise by the action of the spring 248. In this case, the hook member 242 functions as a strut between the main unit of the rotation portion 232 and the operation panel to inhibit counterclockwise rotation of the rotation portion 232. Then, by pushing the outer surface of the hook member 242 to place the hook member 242 in a fallen state, it is possible to rotate the rotational member 232 counterclockwise to thereby restore the display restraint mechanism 228 in the unactuated state. In this state, it is possible to pull the handle main unit 32A upward out of the receiving groove 234. Here, while in the state in which the display unit is restrained, the display unit is in a substantially vertical state, the display unit may be slightly inclined forward.

In the present embodiment, as the display unit restraint mechanism 228 is disposed in a triangular gap space at the back side of the operation panel, there can be achieved advantages that the dead space can be effectively used and that the display unit restraint mechanism 28 can be placed out of sight of the user who is sitting so as to make the appearance of the device preferable. As a matter of course, when the user is standing, it is possible for the user to visually recognize the display unit restraint mechanism 228, and it is also easy to insert the user's hand into the triangular gap space.

Figure 25:
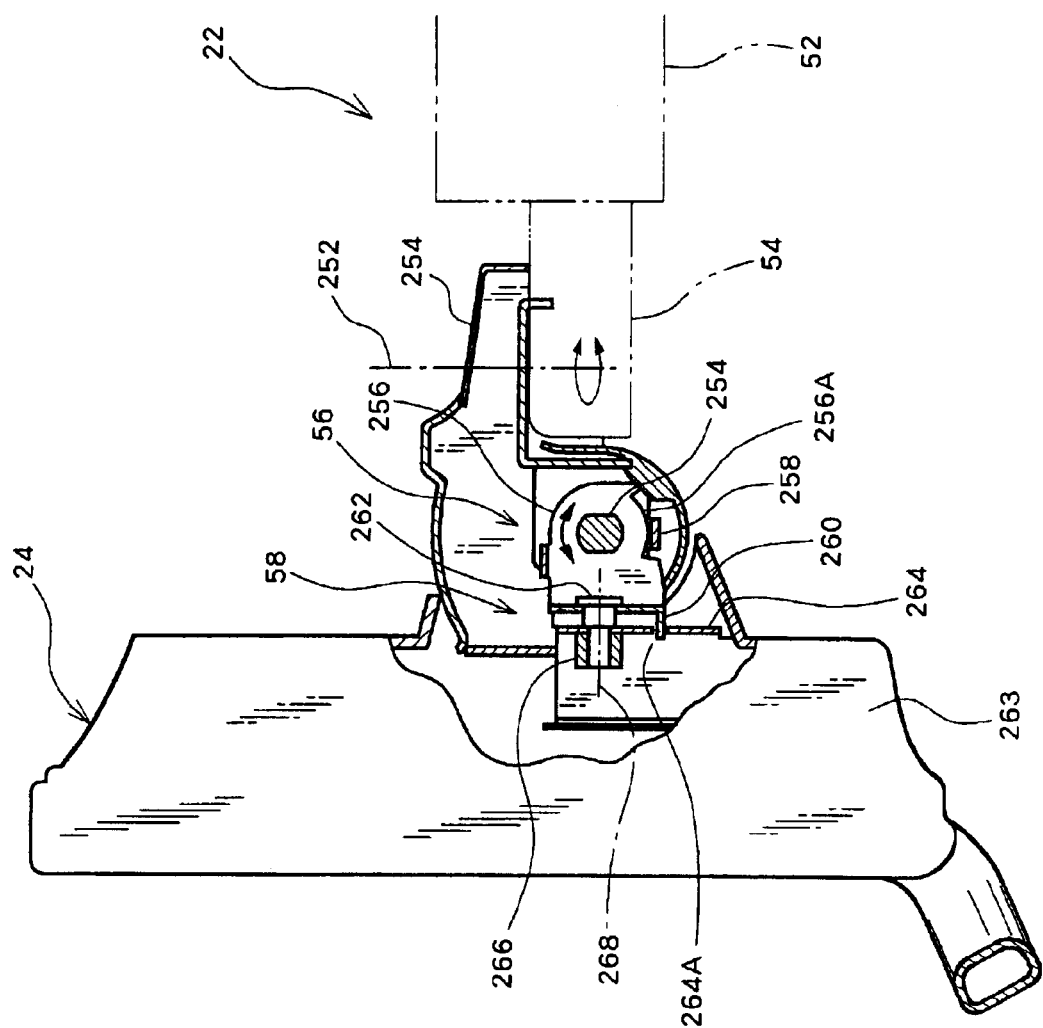
FIG. 25 Partial cross sectional view illustrating an attitude correction mechanism.
Figure 26:
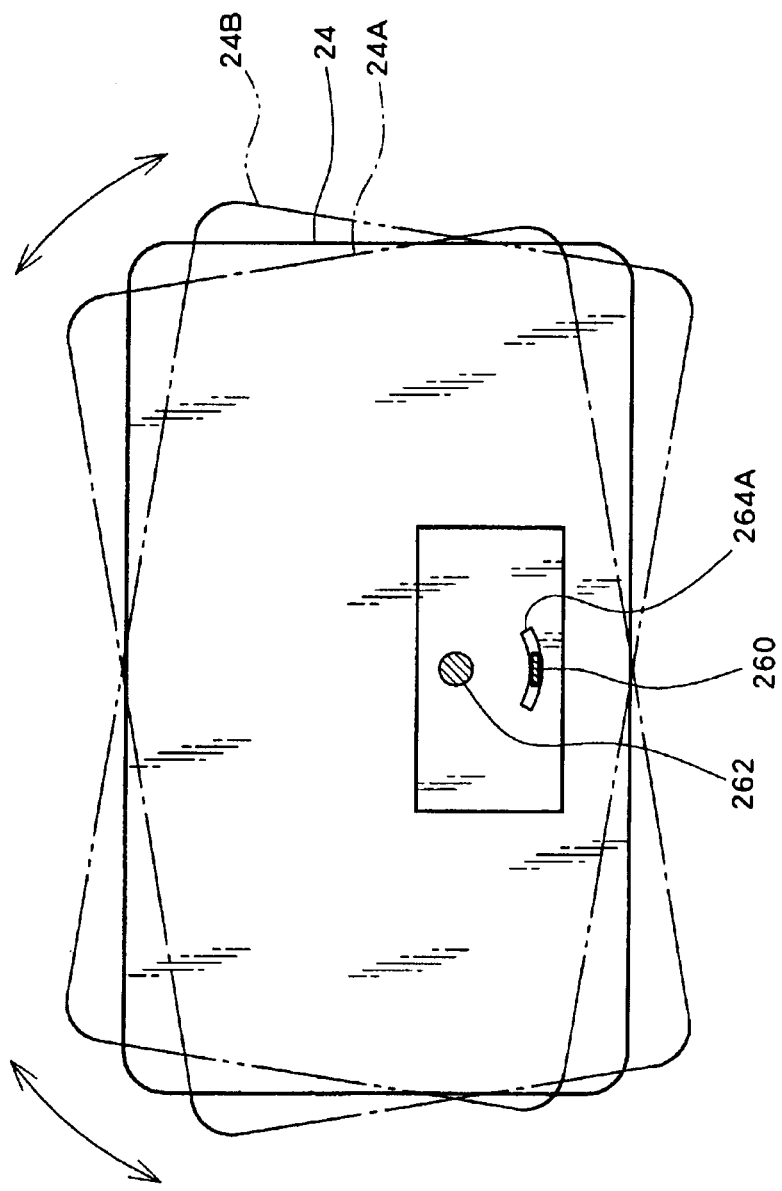
FIG. 26 View for explaining an operation of the attitude correction mechanism.
Figure 27:
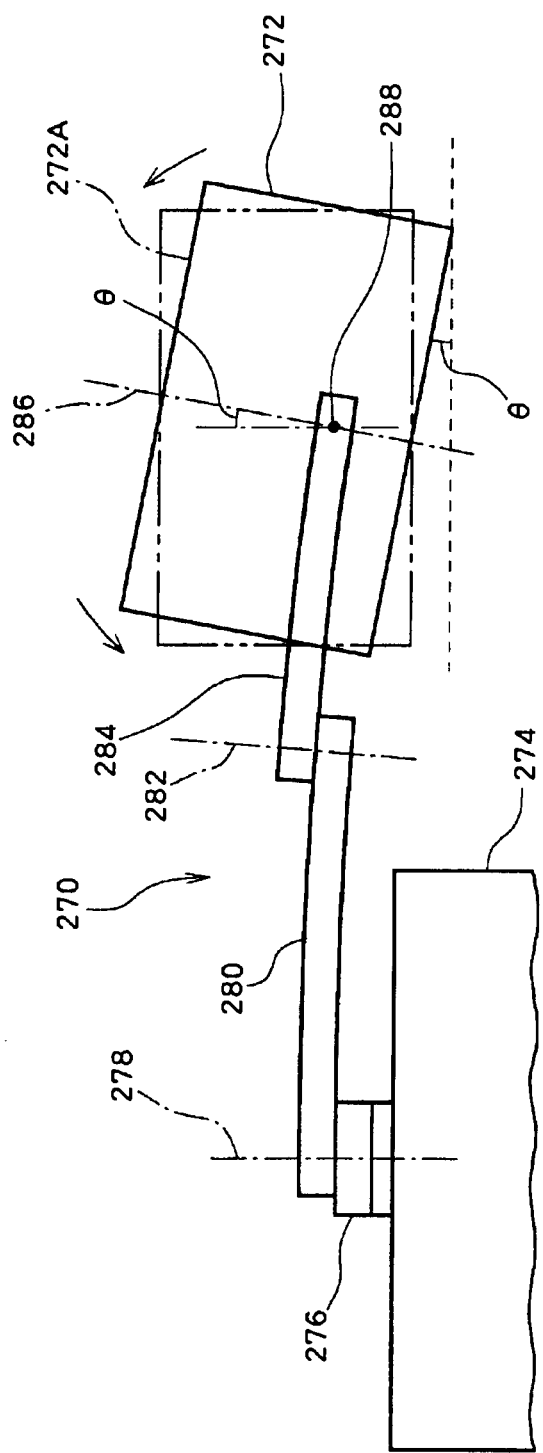
FIG. 27 View for explaining inclination of the display unit due to drooping down of a motion end of an arm array.

(7) Attitude Correction Mechanism (FIGS. 25 to 27)

Next, the attitude correction mechanism will be described with reference to FIGS. 25 to 27. FIG. 25 illustrates a portion of the arm mechanism 22; more specifically, schematically illustrates the second arm 52 and the third pivot portion 54. Reference numeral 252 indicates a pivot center axis in the third pivot portion 54. The tilt portion 56 is coupled to the third pivot portion 54. The tilt portion 56 is disposed within the cover 254 and includes a tilt axis 254 as a horizontal axis. A fitting 256 is coupled to the tilt axis 254. A slot 256A is formed on the lower side of the fitting 256, and a side prong 258 coupled to the third pivot portion 54 is placed within the slot 256A. As such, due to the contact relationship between the slot 256A and the side prong 258, a limitation is imposed on the maximum tilt rotational angle in the tilt portion 56.

The attitude correction mechanism 58 is illustrated between the tilt portion 56 and the display unit 24. The attitude correction mechanism 58 includes a shaft member 262 provided on the front plate of the fitting 256. The shaft member 262 is coupled to a frame 264 provided within the case 263 of the display unit 24. Reference numeral 268 indicates a correction movement center axis. Due to the engaging relationship between the shaft member 262 and a bearing 266, the display unit 24 can perform rotational movement in both directions about the correction movement center axis 268 with the maximum angle being ±5 degrees, for example. Such a correction rotation range can be determined arbitrarily. In the present embodiment, as will be described in detail below, because the attitude correction mechanism 58 is provided in order to eliminate an apparent rotation of the display unit 24 resulting from drooping of the end portion of the arm mechanism, the maximum correction angle is desirably selected to be within a range of ±2 to ±20 degrees, and more desirably within a range of ±2 to ±10 degrees. As it becomes difficult to protect the interior members if too large a rotational movement is permitted, such a degree of the correction angle range as described above is desirable. However, a ±90 degrees rotational mechanism may be provided. The frame 264 includes an arc-shape slit 264A extending in the left-right direction formed therein, and a forward prong 260 which is a portion of the fitting 256 is inserted in the slit 264A. Specifically, with the relative rotational movement of the display unit 24, the forward prong 260 moves in the left-right direction within the slit 264A, and further rotation of the display unit 24 is inhibited when the forward prong 260 reaches the left and right ends of the slit 264A.

In the structure illustrated in FIG. 25, as the correction movement center axis 268 passes through the horizontal tilt center axis of the tilt axis 254, the correction movement center axis 268 and the tilt axis 254 are in an orthogonal relationship. With such a structure, it is easy to hold the display unit 24 with both hands to allow the display unit 24 to perform the tilt movement and the rotation movement simultaneously. In the present embodiment, the attitude correction mechanism 58 is provided as a portion of the arm mechanism 22. More specifically, the attitude correction mechanism 58 is provided in order to solve the problem of an apparent rotation of the display unit caused by the arm mechanism main unit in the arm mechanism 22.

FIG. 26 illustrates an action of the attitude correction mechanism. Reference numeral 262 indicates the shaft member, and FIG. 26 further illustrates a fitting relationship between the slit 264A having an arc shape and the forward prong 260. Reference numeral 24 indicates the display unit, and in the present embodiment, it is possible to cause the display unit 24 to rotate in both the clockwise and counterclockwise directions about the shaft member 262. These states are illustrated by reference numerals 24A and 24B.

FIG. 27 illustrates a specific action of the attitude correction mechanism. A base 276 is provided on a main unit 274, and an arm mechanism 270 is mounted on the base 276. The arm mechanism 270 includes a plurality of pivot mechanisms and a plurality of arm mechanisms, and reference numerals 278, 282, and 286 indicate pivot axes. Further, as the plurality of arms, a first arm 280 and a second arm 284 are illustrated. In FIG. 27, warp or drooping of the end portion caused by these arms 280 and 284 or the pivot mechanisms is illustrated in an exaggerated manner. Specifically, with respect to the vertical pivot axis 278, the pivot axis 282 is slightly inclined, and the pivot axis 286 is largely inclined at an inclination angle of θ.

Consequently, the end portions of the plurality of arms droop down, which makes the display unit 272, which is mounted at a correct angle with respect to the end portion, appear to be rotated or drooping down. Such a problem is likely to occur when the plurality of arms are extended to a great degree toward the right or left side of the main unit. When such drooping occurs, the upper edge and the lower edge of the display unit 272 are inclined with respect to the horizontal level by the angle θ. Such a state is not desirable to the user, who may feel uncomfortable or uneasy. Accordingly, in the present embodiment, it is possible to cause the display unit 272 to slightly rotate about a correction movement center axis 288; more specifically, the attitude of the display unit can be corrected to the attitude which is parallel to the vertical line, as indicated by reference numeral 272A. As a result, even if drooping occurs in the arm mechanism, the display unit itself is parallel to the horizontal line, whereby the uncomfortable or uneasy feeling felt by the user can be eliminated.

By providing the attitude correction mechanism as described above, even if a predetermined amount of drooping of the end portion is allowed, this does not cause any adverse effects on the user. Thus, an advantage that benefits will accrue in the design or the like of the arm mechanism 270 can be obtained. As a matter of course, it is not necessary to actually operate the attitude correction mechanism if no such drooping problems occur. Further, if the user feels no discomfort, the display unit 272 which appears to rotate may be used in such a condition.

REFERENCE SYMBOLS 10 ultrasonic diagnosis device, 12 main unit, 14 movable section, 16 movable mechanism, 18 operation panel, 20 base, 22 arm mechanism, 24 display unit, 42 handle, 58 attitude correction mechanism, 60 lifting mechanism, 62 left-right slide mechanism, 64 forward-backward slide mechanism, 65 rotation limitation mechanism, 66 rotation mechanism, 68 horizontal movement mechanism, 84 shutter mechanism, 136 home position lock mechanism, 228 display unit restraint mechanism.

The invention claimed is:
1. An ultrasonic diagnosis device, comprising:
an operation panel including a plurality of input units for ultrasonic diagnosis;
a base that is provided on a back side of the operation panel;
an arm mechanism that is mounted on the base;
a display unit that is movably supported by the arm mechanism and includes a handle that is to be held by a user; and
a display unit restraint mechanism that is provided on the base or the operation panel to detachably hold the handle to thereby restrain the display unit, wherein
the handle includes a rod-like handle main portion provided on a lower portion on a front surface side of the display unit and extending along a left-right direction of the display unit,
the display unit restraint mechanism includes:
a handle groove opened upwardly to receive the handle main portion; and
a cover member covering over an upper side of the handle main portion when the handle main portion is fitted into the handle groove, and
said detachably holding the handle to thereby restrain the display unit is defined by the handle main portion being fitted into the handle groove with the cover member covering the upper side of the handle main portion to hold the handle and thereby restrain the display unit and the handle being detachable upwardly from the handle groove with the cover member retracted to expose the upper side of the handle main portion.
2. The ultrasonic diagnosis device according to claim 1, wherein the display unit restraint mechanism further includes a restriction member that restricts return of the cover member when the cover member is in a covering state in which the cover member covers over the upper side of the handle main portion.

3. The ultrasonic diagnosis device according to claim 2, wherein
the operation panel is composed of a first operation section provided on a front side and a second operation section that stands upright from a back side of the first operation section;
the base includes an extension end that is coupled with a rear surface of the second operation section; and
the display unit restraint mechanism is disposed in a space formed between an upper surface of the extension end and the rear surface of the second operation section.

4. The ultrasonic diagnosis device according to claim 3, wherein
the restriction member restricts a returning movement of the cover member by mechanically coupling the cover member in the covering state with an upper portion of the second operation section.

5. The ultrasonic diagnosis device according to claim 4, wherein
the cover member is a member that performs a rotation movement about a horizontal center axis;
the restriction member is housed in the cover member in an unactuated state thereof and protrudes outward from within the cover member to serve as a strut between the cover member and the upper portion of the second operation section; and
an urging member for urging the restriction member in a protruding direction is provided.

6. An ultrasonic diagnosis device comprising:
a housing that houses an electronic circuit for ultrasonic diagnosis;
an arm mechanism that is provided on the housing;
a display unit that is movably supported by the arm mechanism and includes a handle that is to be held by a user; and
a display unit restraint mechanism that is provided on the housing or a movable member movably supported by the housing, the display unit restraint mechanism detachably holding the handle to restrain the display unit, wherein
the handle includes a rod-like handle main portion provided on a lower portion on a front surface side of the display unit and extending along a left-right direction of the display unit,
the display unit restraint mechanism includes:
a handle groove opened upwardly to receive the handle main portion; and
a cover member covering over an upper side of the handle main portion when the handle main portion is fitted into the handle groove, and
said detachably holding the handle to restrain the display unit is defined by the handle main portion being fitted into the handle groove with the cover member covering the upper side of the handle main portion to hold the handle and restrain the display unit and the handle being detachable upwardly from the handle groove with the cover member retracted to expose the upper side of the handle main portion.

7. An ultrasonic diagnosis device comprising:
a housing that houses an electronic circuit for ultrasonic diagnosis;
an arm mechanism that is provided on the housing;
a display unit that is movably supported by the arm mechanism and includes a handle that is to be held by a user, the handle including a rod-like handle main portion provided on a lower portion on a front surface side of the display unit and extending along a left-right direction of the display unit; and
a display unit restraint mechanism that is provided on the housing or a movable member movably supported by the housing, the display unit restraint mechanism detachably holding the handle to restrain the display unit, the display unit restraint mechanism including a receiving port defining a handle groove opening upwardly for receiving the handle main portion and a cover member extending underneath the receiving port when the handle groove is opened for receiving the handle main portion and movable from underneath the receiving port to wrap over an upper side of the handle main portion when the handle main portion is fitted into the handle groove, wherein said detachably holding the handle to restrain the display unit is defined by the handle main portion being fitted into the handle groove with the cover member covering the upper side of the handle main portion to hold the handle and restrain the display unit and the handle being detachable upwardly from the handle groove with the cover member retracted to expose the upper side of the handle main portion.

\* \* \* \* \*